United States Patent
Chen et al.

(10) Patent No.: US 10,400,242 B2
(45) Date of Patent: Sep. 3, 2019

(54) METHODS FOR TREATING ACUTE MYELOID LEUKEMIA AND NANOPARTICLE COMPLEXES OF MIR-22 UTILIZED THEREIN

(71) Applicant: University of Cincinnati, Cincinnati, OH (US)

(72) Inventors: Jianjun Chen, Cincinnati, OH (US); Xi Jiang, Cincinnati, OH (US)

(73) Assignee: University of Cincinnati, Cincinnati, OH (US)

(*) Notice: Subject to any disclaimer, the term of this patent is extended or adjusted under 35 U.S.C. 154(b) by 0 days.

(21) Appl. No.: 15/803,190

(22) Filed: Nov. 3, 2017

(65) Prior Publication Data

US 2018/0119150 A1 May 3, 2018

Related U.S. Application Data

(60) Provisional application No. 62/416,829, filed on Nov. 3, 2016.

(51) Int. Cl.
- *C07H 21/02* (2006.01)
- *C07H 21/04* (2006.01)
- *C12N 15/11* (2006.01)
- *A61K 48/00* (2006.01)
- *C12N 15/113* (2010.01)
- *A61P 35/02* (2006.01)
- *A61K 47/59* (2017.01)
- *A61K 47/64* (2017.01)
- *A61K 31/713* (2006.01)
- *A61K 31/203* (2006.01)
- *A61K 9/00* (2006.01)

(52) U.S. Cl.
CPC ........ *C12N 15/1135* (2013.01); *A61K 9/0019* (2013.01); *A61K 31/203* (2013.01); *A61K 31/713* (2013.01); *A61K 47/595* (2017.08); *A61K 47/64* (2017.08); *A61P 35/02* (2018.01); *C12N 15/113* (2013.01); *C12N 2310/141* (2013.01); *C12N 2310/321* (2013.01); *C12N 2320/31* (2013.01); *C12N 2320/32* (2013.01)

(58) Field of Classification Search
CPC .... A61K 31/7088; A61K 38/17; A61K 38/19; A61K 38/20; A61K 39/00; A61K 31/713; C12N 15/113; C12N 15/1135; C12N 2310/141; C12N 2310/321; A61P 35/02
See application file for complete search history.

(56) References Cited

U.S. PATENT DOCUMENTS 7,534,867 B1 * 5/2009 Hannum ................ A61K 38/02
424/85.1

OTHER PUBLICATIONS

Jiang et al. (Blood Dec. 3, 2015 vol. 126, No. 23, pp. 3784, Abstract).*

(Continued)

*Primary Examiner* — Terra C Gibbs
(74) *Attorney, Agent, or Firm* — Dinsmore & Shohl LLP

(57) ABSTRACT

Compositions and methods for treating acute myeloid leukemia (AML) based on upregulating expression of microRNA-22 (miR-22), and a nanoparticle delivery system that utilizes FLT3-functionalized polyamidoamine (PAMAM) dendromirs for targeted delivery of miR-22 and/or agents that upregulate expression of miR-22 to AML cells.

24 Claims, 25 Drawing Sheets
(18 of 25 Drawing Sheet(s) Filed in Color)

Specification includes a Sequence Listing.

(56) References Cited

OTHER PUBLICATIONS

Jiang et al. (Blood Dec. 6, 2014 vol. 124 No. 21, pp. 886, Abstract).*
Mermel CH, Schumacher SE, Hill B, Meyerson ML, Beroukhim R, Getz G. GISTIC2.0 facilitates sensitive and confident localization of the targets of focal somatic copy-number alteration in human cancers. Genome Biol 12, R41 (2011).
Parkin B, et al. NF1 inactivation in adult acute myelogenous leukemia. Clin Cancer Res 16, 4135-4147 (2010).
Parkin B, et al. Acquired genomic copy number aberrations and survival in adult acute myelogenous leukemia. Blood 116, 4958-4967 (2010).
Saeed Al, et al. TM4 microarray software suite. Methods Enzymol 411, 134-193 (2006).
Estey E, Dohner H. Acute myeloid leukaemia. Lancet 368, 1894-1907 (2006).
Grimwade D, Mrozek K. Diagnostic and prognostic value of cytogenetics in acute myeloid leukemia. Hematology/oncology clinics of North America 25, 1135-1161, vii (2011).
Chen J, Odenike O, Rowley JD. Leukaemogenesis: more than mutant genes. Nat Rev Cancer 10, 23-36 (2010).
Graubert T, Walter MJ. Genetics of myelodysplastic syndromes: new insights. Hematology Am Soc Hematol Educ Program 2011, 543-549 (2011).
Figueroa ME, et al. MDS and secondary AML display unique patterns and abundance of aberrant DNA methylation. Blood 114, 3448-3458 (2009).
Griffiths EA, Gore SD. Epigenetic therapies in MDS and AML. Adv Exp Med Biol 754, 253-283 (2013).
Hu X, et al. Tet and TDG mediate DNA demethylation essential for mesenchymal-to-epithelial transition in somatic cell reprogramming. Cell Stem Cell 14, 512-522 (2014).
Delhommeau F, et al. Mutation in TET2 in myeloid cancers. N Engl J Med 360, 2289-2301 (2009).
Ko M, et al. Impaired hydroxylation of 5-methylcytosine in myeloid cancers with mutant TET2. Nature 468, 839-843 (2010).
Moran-Crusio K, et al. Tet2 loss leads to increased hematopoietic stem cell self-renewal and myeloid transformation. Cancer Cell 20, 11-24 (2011).
Huang H, et al. TET1 plays an essential oncogenic role in MLL-rearranged leukemia. Proc Natl Acad Sci U S A 110, 11994-11999 (2013).
Song SJ, et al. The oncogenic microRNA miR-22 targets the TET2 tumor suppressor to promote hematopoietic stem cell self-renewal and transformation. Cell Stem Cell 13, 87-101 (2013).
Jiang X, et al. Blockade of miR-150 Maturation by MLL-Fusion/MYC/LIN-28 is Required for MLL-Associated Leukemia. Cancer Cell 22, 524-535 (2012).
Lewis BP, Burge CB, Bartel DP. Conserved seed pairing, often flanked by adenosines, indicates that thousands of human genes are microRNA targets. Cell 120, 15-20 (2005).
Gurha P, et al. Targeted deletion of microRNA-22 promotes stress-induced cardiac dilation and contractile dysfunction. Circulation 125, 2751-2761 (2012).
He C, Li Z, Chen P, Huang H, Hurst LD, Chen J. Young intragenic miRNAs are less coexpressed with host genes than old ones: implications of miRNA-host gene coevolution. Nucleic Acids Res 40, 4002-4012 (2012).
Ley TJ, et al. Genomic and epigenomic landscapes of adult de novo acute myeloid leukemia. N Engl J Med 368, 2059-2074 (2013).
Li Z, et al. miR-196b directly targets both HOXA9/MEIS1 oncogenes and FAS tumour suppressor in MLL-rearranged leukaemia. Nat Commun 2, 688 (2012).
Cheng JC, et al. CREB is a critical regulator of normal hematopoiesis and leukemogenesis. Blood 111, 1182-1192 (2008).
Sandoval S, Pigazzi M, Sakamoto KM. CREB: A Key Regulator of Normal and Neoplastic Hematopoiesis. Adv Hematol 2009, 634292 (2009).

Haferlach C, et al. ETV6 rearrangements are recurrent in myeloid malignancies and are frequently associated with other genetic events. Genes Chromosomes Cancer 51, 328-337 (2012).
Armstrong SA, et al. Inhibition of FLT3 in MLL. Validation of a therapeutic target identified by gene expression based classification. Cancer Cell 3, 173-183 (2003).
Pigazzi M, et al. MicroRNA-34b promoter hypermethylation induces CREB overexpression and contributes to myeloid transformation. Haematologica 98, 602-610 (2013).
Placke T, et al. Requirement for CDK6 in MLL-rearranged acute myeloid leukemia. Blood 124, 13-23. (2014).
Ayton PM, Cleary ML. Transformation of myeloid progenitors by MLL oncoproteins is dependent on Hoxa7 and Hoxa9. Genes Dev 17, 2298-2307 (2003).
Schwable J, et al. RGS2 is an important target gene of Flt3-ITD mutations in AML and functions in myeloid differentiation and leukemic transformation. Blood 105, 2107-2114 (2005).
Smith LL, et al. Functional crosstalk between Bmi1 and MLL/Hoxa9 axis in establishment of normal hematopoietic and leukemic stem cells. Cell Stem Cell 8, 649-662 (2011).
Jacoby MA, Walter MJ. Detection of copy number alterations in acute myeloid leukemia and myelodysplastic syndromes. Expert Rev Mol Diagn 12, 253-264 (2012).
Ninomiya S, et al. Integrated analysis of gene copy number, copy neutral LOH, and microRNA profiles in adult acute lymphoblastic leukemia. Cytogenet Genome Res 136, 246-255 (2012).
Konishi H, et al. Detailed characterization of a homozygously deleted region corresponding to a candidate tumor suppressor locus at distal 17p13.3 in human lung cancer. Oncogene 22, 1892-1905 (2003).
Sankar M, et al. Identification of a commonly deleted region at 17p13.3 in leukemia and lymphoma associated with 17p abnormality. Leukemia 12, 510-516 (1998).
Chattopadhyay P, Rathore A, Mathur M, Sarkar C, Mahapatra AK, Sinha S. Loss of heterozygosity of a locus on 17p13.3, independent of p53, is associated with higher grades of astrocytic tumours. Oncogene 15, 871-874 (1997).
Li Z, et al. Identification of a 24-gene prognostic signature that improves the European LeukemiaNet risk classification of acute myeloid leukemia: an international collaborative study. J Clin Oncol 31, 1172-1181 (2013).
Bar N, Dikstein R. miR-22 forms a regulatory loop in PTEN/AKT pathway and modulates signaling kinetics. PLoS One 5, e10859 (2010).
Drach J, Lopez-Berestein G, McQueen T, Andreeff M, Mehta K. Induction of differentiation in myeloid leukemia cell lines and acute promyelocytic leukemia cells by liposomal all-trans-retinoic acid. Cancer Res 53, 2100-2104 (1993).
Duan Z, Horwitz M. Targets of the transcriptional repressor oncoprotein Gfi-1. Proc Natl Acad Sci USA 100, 5932-5937 (2003).
Pack DW, Hoffman AS, Pun S, Stayton PS. Design and development of polymers for gene delivery. Nat Rev Drug Discov 4, 581-593 (2005).
Cartron PF, Nadaradjane A, Lepape F, Lalier L, Gardie B, Vallette FM. Identification of TET1 Partners That Control its DNA-Demethylating Function. Genes Cancer 4, 235-241 (2013).
Saleque S, Kim J, Rooke HM, Orkin SH. Epigenetic regulation of hematopoietic differentiation by Gfi-1 and Gfi-1b is mediated by the cofactors CoREST and LSD1. Mol Cell 27, 562-572 (2007).
Abdel-Wahab O, et al. Genetic characterization of TET1, TET2, and TET3 alterations in myeloid malignancies. Blood 114, 144-147 (2009).
Huang MJ, Cheng YC, Liu CR, Lin S, Liu HE. A small-molecule c-Myc inhibitor, 10058-F4, induces cell-cycle arrest, apoptosis, and myeloid differentiation of human acute myeloid leukemia. Exp Hematol 34, 1480-1489 (2006).
Ling H, Fabbri M, Cahn GA. MicroRNAs and other non-coding RNAs as targets for anticancer drug development. Nat Rev Drug Discov 12, 847-865 (2013).
Li Z, et al. Distinct microRNA expression profiles in acute myeloid leukemia with common translocations. Proc Natl Acad Sci U S A 105, 15535-15540 (2008).

(56) References Cited

OTHER PUBLICATIONS

Irizarry RA, Bolstad BM, Collin F, Cope LM, Hobbs B, Speed TP. Summaries of Affymetrix GeneChip probe level data. Nucleic Acids Res 31, e15 (2003).

Poliseno L, et al. Identification of the miR-106b-~25 microRNA cluster as a proto-oncogenic PTEN-targeting intron that cooperates with its host gene MCM7 in transformation. Sci Signal 3, ra29 (2010).

Krivtsov AV, et al. Transformation from committed progenitor to leukaemia stem cell initiated by MLL-AF9. Nature 442, 818-822 (2006).

Somervaille TC, et al. Hierarchical maintenance of MLL myeloid leukemia stem cells employs a transcriptional program shared with embryonic rather than adult stem cells. Cell Stem Cell 4, 129-140 (2009).

Sekeres MJ, et al. Increasing CRTC1 function in the dentate gyrus during memory formation or reactivation increases memory strength without compromising memory quality. J Neurosci 32, 17857-17868 (2012).

Jiang X, Yang P, Ma L. Kinase activity-independent regulation of cyclin pathway by GRK2 is essential for zebrafish early development. Proc Natl Acad Sci U S A 106, 10183-10188 (2009).

Modi DA, Sunoqrot S, Bugno J, Lantvit DD, Hong S, Burdette JE. Targeting of follicle stimulating hormone peptide-conjugated dendrimers to ovarian cancer cells. Nanoscale 6, 2812-2820 (2014).

Xi Jiang et al, miR-22 has a potent anti-tumor role with therapeutic potential in acute myeloid leukemia, Nature Communications, Apr. 26, 2016; 7:11452; DOI: 10.1038/ncomms11452/www.nature.com/naturecommunications.

Johannes Zuber et al, RNAi screen identifies Brd4 as a therapeutic target in acute myeloid leukemia, Nature 478 (7370): 524-528; Apr. 17, 2012.

Bernd B. Zeisig et al, SnapShot: Acute Myeloid Leukemia, Cancer Cell, 22, Nov. 13, 2012; DOI 10.1016/j.ccr.2012/10.017.

Ming Yan et al, A previously unidentified alternatively spliced isoform of t(8;21) transcript promotes leukemogenesis, Nature Medicine, vol. 12, No. 8, Aug. 2006, 945-949.

Bernd B. Zeisig et al, Hoxa9 and Meis1 are Key Targets for MLL-ENL-Mediated Cellular Immortalization; Molecular and Cellular Biology, Jan. 2004, pp. 617-628.

Jianhua Xiong et al, Tumor-suppressive microRNA-22 inhibits the transcription of E-box-containing c-Myc target genes by silencing c-Myc; Oncogene, Sep. 2010, DOI: 10.1038/onc.2010.241.

Yi Xu et al, The HMG-I Oncogene causes Highly Penetrant, Aggressive Lymphoid Malignancy in Transgenic Mice and is Overexpressed in Human Leukemia; Cancer Research, 64, 3371-3375; May 15, 2004.

M. Wunderlich et al, AML xenograft efficiency is significantly improved in NOD-SCID-IL2RG mice constitutively expressing human SCF, GM-CSF and IL-3; Leukemia, Oct. 2010; 24(10): 1785-1788.

Hao Wu et al, Dual functions of Tet1 in transcriptional regulation in mouse embryonic stem cells; Nature, vol. 473, May 19, 2011; pp. 389-394.

Xi Wu et al, Molecular mechanisms of fatty acid synthase (FASN)-mediated resistance to anti-cancer treatments; Advances in Biological Regulation 54 (2014) 214-221.

Kristine Williams et al, Tet1 and hydroxymethylcytosine in transcription and DNA methylation fidelity; Nature; May 19, 2011; 473(7347): 343-348.

Peter Van Loo et al, Allele-specific copy number analysis of tumors; PNAS; Sep. 28, 2010; vol. 107, No. 39, 16910-16915.

Zhong Wang et al, GSK-3 promotes conditional association of CREB and its co-activators with MEIS1 to facilitate HOX-mediated transcription and oncogenesis; Cancer Cell, Jun. 15, 2010; 17(6): 597-608.

Kai Wang et al, PennCNV: An integrated hidden Markov model designed for high-resolution copy number variation detection in whole-genome SNP genotyping data; Genome Research, 2007; 17: 1665-1674.

Su Jung Song et al, MicroRNA-Antagonism Regulates Breast Cancer Stemness and Metastasis via TET-Family-Dependent Chromatin Remodeling; Cell 154, 311-324, Jul. 18, 2013.

Roshana Thambyrajah et al, GFI1 proteins orchestrate the emergence of hematopoietic stem cells through recruitment of LSD1; Nature Cell Biology; Nov. 30, 2015; DOI: 10.1038/ncb3276.

Shinichiro Takahashi, Downstream molecular pathways of FLT3 in the pathogenesis of acute myeloid leukemia: biology and therapeutic implications; Journal of Hematology & Oncology, 2011, 4:13.

\* cited by examiner

Fig. 3G

```
                      518  (SEQ ID NO: 25)                  720
CRTC1-3'UTR      ...CAGTGGCAGCTGAGACCTCT...CCTTCTTGGCAGCTCAGGG... (SEQ ID NO: 26)
              (SEQ ID NO: 27)  |||||||                |||||||
miR-22           UGUCAAGAAGUUGACCGUCGAA  UGUCAAGAAGUUGACCGUCGAA (SEQ ID NO: 27)

CRTC1-3'UTRmut   ...CAGAAATTATAGAGACCTCT...CCTTCTAAATTATACAGGG... (SEQ ID NO: 29)
                    (SEQ ID NO: 28)

571                                   613
FLT3-3'UTR       ...CAAGGAATGTGTAGGCAGCTATGGTTGTCACAG... (SEQ ID NO: 30)
                                  |||||||
miR-22              UGUCAAGAAGUUGACCGUCGAA (SEQ ID NO: 27)

FLT3-3'UTRmut    ...CAAGGAATGTGTATTACTAGGATGGTTGTCACAG... (SEQ ID NO: 31)
```

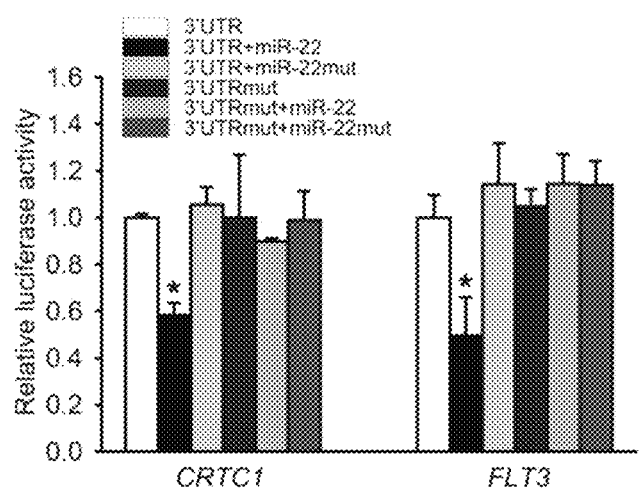

Fig. 3H

METHODS FOR TREATING ACUTE MYELOID LEUKEMIA AND NANOPARTICLE COMPLEXES OF MIR-22 UTILIZED THEREIN

PRIORITY CLAIM

This application claims priority to U.S. Provisional application Ser. No. 62/416,829, filed Nov. 3, 2016, the entire disclosure of which is incorporated herein.

GOVERNMENT INTERESTS

This invention was made with government support under Contract Nos. R01 CA178454, R01 CA182528, and R01 CA127277 awarded by the National Institutes of Health. The U.S. government has certain rights in the invention.

BACKGROUND

As one of the most common and fatal forms of hematopoietic malignancies, acute myeloid leukemia (AML) is frequently associated with diverse chromosome translocations (e.g. t(11q23)/MLL-rearrangements, t(15; 17)/PML-RARA and t(8;21)/AML1-ETO) and molecular abnormalities (e.g. internal tandem duplications of FLT3 (FLT3-ITD) and mutations in nucleophosmin (NPM1c$^+$))[1]. Despite intensive chemotherapies, the majority of patients with AML fail to survive longer than 5 years[2, 3]. Thus, development of effective therapeutic strategies based on a better understanding of the molecular mechanisms underlying the pathogenesis of AML is urgently needed.

MicroRNAs (miRNAs) are a class of small, non-coding RNAs that post-transcriptionally regulate gene expression[4]. Individual miRNAs may play distinct roles in cancers originating from different tissues or even from different lineages of hematopoietic cells[4]. It is unclear whether a single miRNA can play distinct roles between malignancies originating from the same hematopoietic lineage, such as de novo AML and myelodysplastic syndrome (MDS). Although around 30% of MDS cases transform to AML, the genetic and epigenetic landscapes of MDS or MDS-derived AML are largely different from those of de novo AML[5, 6]. For example, it is known that MDS and MDS-derived AML are more responsive to hypomethylating agents than de novo AML[7]. The molecular mechanisms underlying the distinct pathogenesis and drug response between MDS (or MDS-derived AML) and de novo AML remain unclear.

The ten-eleven translocation (Tet1/2/3) proteins play critical transcriptional regulatory roles in normal developmental processes as activators or repressors[8, 9, 10] ENREF 5. In contrast to the frequent loss-of-function mutations and tumor-suppressor role of TET2 observed in hematopoietic malignancies[11, 12, 13], the present investigators recently reported that TET1 plays an essential oncogenic role in MLL-rearranged AML where it activates expression of homeobox genes[14]. However, it is unknown whether TET1 can also function as a transcriptional repressor in cancer. Moreover, Tet1-mediated regulation of miRNA expression has rarely been studied[10].

Investigation of Tet1-mediated regulation of miRNA expression provides a novel pathway for addressing the urgent need for additional and/or complementary treatments for AML.

SUMMARY

Accordingly, the present investigators uncovered a TET1/GFI1/EZH2/SIN3A⊣miR-22⊣CREB-MYC signaling circuit in de novo AML, in which miR-22 functions as a pivotal anti-tumor gate-keeper, distinct from its oncogenic role reported in MDS or MDS-derived AML[16], and further, developed novel miR-22-based therapies to treat AML patients. Embodiments provide nanoparticles complexed with miR-22 and designed to target AML cells and which are shown to significantly inhibit AML progression and prolong survival of leukemic mice. Summarily, agents, compositions and methods that restore miR-22 expression/function (e.g., using miR-22-carrying nanoparticles or small-molecule compounds) and exhibit therapeutic efficacy in the treatment of AML, especially those resistant to current therapies, are disclosed.

One embodiment provides methods of treating a patient suffering from acute myeloid leukemia (AML), and in particular, de novo AML. The methods comprise: administering to the patient at least one agent that upregulates expression of miR-22. According to other embodiments, miR-22 may be administered directly to the patient, for example by utilizing a nanoparticle delivery system. According to one embodiment, methods of treating a patient suffering from acute myeloid leukemia comprise administering G7-Flt3L-(2'OMe)miR-22 to the patient.

Another embodiment is directed to a nanoparticle delivery system designed for sustained delivery of microRNA-22 (miR-22) to acute myeloid leukemia (AML) cells, the nanoparticle delivery system comprising poly(amidoamine) (PAMAM) dendrimers complexed with miR-22, wherein at least one dendrimer is surface-functionalized with a ligand specific for FLT3 receptor.

Another embodiment provides pharmaceutical compositions, for example, formulated as an injectable composition, comprising a nanoparticle delivery system designed for targeted and sustained delivery of microRNA-22 (miR-22) to acute myeloid leukemia (AML) cells, the nanoparticle delivery system comprising PAMAM dendrimers complexed with miR-22, wherein at least one dendrimer is surface-functionalized with a ligand specific for FLT3 receptor.

These and other embodiments and aspects will be detailed and clarified by reference to the Figures and Detailed Description, below.

Figures are provided to illustrate particular aspects and features of different embodiments and should not be construed as limiting the full scope of the invention as defined by the appended claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 1A Exiqon microRNA profiling assay showing that miR-22 is significantly (p<0.05) down-regulated in the entire AML set (n=85); FIG. 1B or in each individual subset relative to normal controls (the expression data were log(2) transformed and mean-centered with mean±SEM values shown; FIG. 1C sets forth a comparison of effects of in-house miR-22, miR-22_Song[16] and miR-22 mutant (miR-22mut, mutation sequence at the top) on MLL-AF9-induced colony formation (colony-forming/replating assays (CFAs) were performed using mouse BM progenitor (Lin$^-$) cells transduced with MSCV-neo+ MSCV-PIG (Ctrl), MSCV-neo-MLL-AF9+MSCV-PIG (MLL-AF9), or MSCV-neo-MLL-AF9+MSCV-PIG-miR- 22/miR-22_Song/miR-22mut; FIG. 1D shows the effects of miR-22 on colony formation induced by multiple fusion genes (CFA was performed using wild-type BM progenitor cells co-transduced with MSCV-neo-MLL-AF9 (MA9), -MLL-AF10 (MA10), -PML-RARA (PR) or -AML1-ETO9a (AE9a)[19], together with MSCV-PIG (Ctrl) or MSCV-PIG-miR-22 (+miR-22), as well as miR-22$^{-/-}$ BM progenitors co-transduced with individual fusion genes and MSCV-PIG, and colony counts (mean±SD) of the second round of plating are shown. *, p<0.05; **, p<0.01); FIG. 1E shows the effect of miR-22 on MLL-AF9-induced primary leukemogenesis (Kaplan-Meier curves are shown for six cohorts of transplanted mice including MSCVneo+MSCV-PIG (Ctrl; n=5), MSCVneo+MSCV-PIG-miR-22 (miR-22; n=5), MSCVneo-MLL-AF9+MSCV-PIG (MA9; n=8), MSCV-neo-MLL-AF9+MSCV-PIG-miR-150 (MA9+miR-150, n=6), MSCVneo-MLL-AF9+MSCV-PIG-miR-22 (MA9+miR-22; n=10), and MSCVneo-MLL-AF9+MSCV-PIG-miR-22mutant (MA9+miR-22mut; n=5); FIG. 1F Wright-Giemsa stained peripheral blood (PB) and bone marrow (BM), and hematoxylin and eosin (H&E) stained spleen and liver of the primary BMT recipient mice at the end point are shown; FIG. 1G shows the effect of miR-22 on MLL-AF10-induced primary leukemogenesis (Kaplan-Meier curves are shown for two cohorts of transplanted mice including MSCVneo-MLL-AF10+MSCV-PIG (MA10; n=5) and MSCVneo-MLL-AF10+MSCV-PIG-miR-22 (MA10+miR-22; n=5)); FIG. 1H demonstrates that miR-22 knockout promotes AE9a-induced leukemogenesis (Kaplan-Meier curves are shown for mice transplanted with wild-type or miR-22$^{-/-}$ BM progenitor cells transduced MSCV-PIG-AE9a (n=5 for each group), the p values were generated by t-test (FIGS. 1A-D) or log-rank test (FIGS. 1E, 1G and 1H).

FIG. 2A Kaplan-Meier curves showing the effect of miR-22 on the maintenance of MLL-AF9-induced AML in secondary BMT recipient mice—the secondary BMT recipients were transplanted with BM blast cells from the primary MLL-AF9 AML mice retrovirally transduced with MSCV-PIG+MSCVneo (MA9-AML+Ctrl; n=7) or MSCV-PIG+MSCVneo-miR-22 (MA9-AML+miR-22; n=10); FIG. 2B Wright-Giemsa or H&E stained PB, BM, spleen and liver of the secondary leukemic mice are shown; FIG. 2C Kaplan-Meier curves and log-rank test showing effect of miR-22 on the maintenance/progression of AML1-ETO9a (AE9a)-induced AML or FIG. 2D FLT3-ITD/NPM1c$^+$-induced AML in secondary BMT recipient mice (n=5 for each group).

FIGS. 3A-3H demonstrate that miR-22 targets CRTC1, FLT3 and MYCBP. FIG. 3A shows down-regulation of CRTC1, FLT3, MYCBP and ETV6 by forced expression of miR-22 in MONOMAC-6 cells detected 48 hours post-transfection of MSCV-PIG (Ctrl) or MSCV-PIG-miR-22 (miR-22); FIG. 3B Crtc1, Flt3, Mycbp and Etv6 levels in MLL-ENL-ERtm cells after withdrawal of 4-OHT for 0, 7 or 10 days; FIG. 3C expression levels of Crtc1, Flt3, Mycbp and Etv6 in mouse BM progenitor cells retrovirally transduced with MSCV-PIG+MSCV-neo (Ctrl), MSCV-PIG-miR-22+MSCV-neo (miR-22), MSCV-PIG+MSCV-neo-MLL-AF9 (MLL-AF9), or MSCV-PIG-miR-22+MSCV-neo-MLL-AF9 (MLL-AF9+miR-22); FIG. 3D shoes expression levels of Crtc1, Flt3, Mycbp and Etv6 in BM blast cells of leukemic mice transplanted with MLL-AF9, MLL-AF9+miR-22 or MLL-AF9+miR-22mut primary leukemic cells; FIG. 3E shows expression levels of Crtc1, Flt3 and Mycbp in BM blast cells of leukemic mice transplanted with MSCV-PIG or MSCV-PIG-miR-22-retrovirally transduced AE9a, or FIG. 3F FLT3-ITD/NPM1c$^+$ primary leukemic cells; FIG. 3G shows the putative miR-22 target sites and mutants in the 3'UTRs of CRTC1 (upper panel) and FLT3 (lower panel); FIG. 3H shows effects of miR-22 on luciferase activity of the reporter gene bearing wild type or mutant 3'UTRs of CRTC1 or FLT3 in HEK293T cells. The mean±SD values from three replicates are shown. *, p<0.05, t-test. Collectively, FIGS. 4A-4G evidence that CRTC1, FLT3 and MYCBP are functionally important targets of miR-22 in AML.

FIG. 5A Correlation between the expression levels of miR-22 and TET1 in three independent AML patient databases. All expression data were log(2) transformed; the data in In-house_81S were also mean-centered. The correlation coefficient (r) and p values were detected by "Pearson Correlation", and the correlation regression lines were drawn with the "linear regression" algorithm. FIG. 5B Expression of pri-, pre- and mature miR-22, and Tet1/2/3 in colony-forming cells of wild type mouse BM progenitors retrovirally transduced with MSCV-neo (Ctrl), MSCVneo-MLL-AF9 (MLL-AF9), MSCVneo-MLL-AF10 (MLL-AF10) or MSCVneo-AE9a (AE9a), or of FLT3-ITD/NPM1c$^+$ mouse BM progenitors transduced with MSCVneo (FLT3-ITD+/NPM1c+). FIG. 5C Expression of miR-22 and Tet1/2/3 in MLL-ENL-ERtm cells. Expression levels were detected at the indicated time points post 4-OHT withdrawal. FIG. 5D Effect of miR-22 overexpression on Tet1 expression in colony-forming cells with MLL-AF9, AE9a, or FLT3-ITD/NPM1c$^+$. FIG. 5E Expression of Tet1 in BM progenitor cells of 6-weeks old miR-22$^{-/-}$ or wild type mice. FIG. 5F Effect of miR-22 overexpression on TET1 expression in THP-1 and KOCL-48 AML cells 48 hours post-transfection. FIG. 5G Expression of pri-, pre- and mature miR-22 in BM progenitor cells of 6-weeks old Tet1$^{-/-}$ or wild-type mice. Mean±SD values are shown. *, p<0.05, t-test.

FIG. 6A Tet1 targets miR-22 promoter region (−1,100/+55 bp), as detected by luciferase reporter assay 48 hours post transfection in HEK293T cells. FIG. 6B Expression of TET1/2/3, EZH2, SIN3A, GFI1 and miR-22 in THP-1 cells 72 hours post-treatment with 1 μM ATRA or DMSO control. FIG. 6C Co-immunoprecipitation assay showing the binding of endogenous GFI1 and TET1 in THP1 cells. FIG. 6D ChIP-qPCR analyses of the promoter region of miR-22 in THP-1 cells 72 hours post-treatment with 1 μM ATRA or DMSO. Upper panel: PCR site on the CpG-enriched region of miR-22 gene locus. Note: miR-22 is coded within the second exon of a long non coding RNA (MIR22HG), which represents the primary transcript of miR-22. Lower panels: Enrichment of MLL-N terminal (for both wild-type MLL and MLL-fusion proteins), MLL-C terminal (for wild-type MLL), TET1, EZH2, SIN3A, GFI1, H3K27me3, H3K4me3 or RNA pol II at miR-22 promoter region. FIG. 6E Expression levels of TET1, EZH2, SIN3A and miR-22 in GFI1 knockdown cells. FIG. 6F ChIP-qPCR analyses of the promoter region of miR-22 in THP-1 cells transduced with GFI1 shRNA or control shRNA. Enrichment of GFI1, TET1, EZH2 and SIN3A are shown. FIG. 6G Effects of knockdown of TET1, EZH2 and/or SIN3A on miR-22 expression. The expression level of miR-22 was detected in THP-1 cells 72 hours post-transfection with siRNAs targeting TET1, EZH2 and/or SIN3A. Mean±SD values are shown. *, $p<0.05$; **, $p<0.01$ (t-test). FIG. 6H Schematic model of the regulatory pathway involving miR-22 in AML and ATRA treatment.

FIG. 7A Primary leukemia BM cells bearing MLL-AF9 or FIG. 7B AE9a were transplanted into sublethally irradiated secondary recipient mice. After the onset of secondary AML (usually 10 days post transplantation), the recipient mice were treated with PBS control, or 0.5 mg/kg miR-22 or miR-22 mutant RNA oligos formulated with G7 PAMAM dendrimer nanoparticles, i.v., every other day, until the PBS-treated control group all died of leukemia. FIG. 7C NSGS mice[49] were transplanted with MV4;11/t(4;11) AML cells. 5 days post-transplantation, these mice started to be treated with PBS control, miR-22 or miR-22 mutant nanoparticles at the same dose as described above. Kaplan-Meier curves are shown; the drug administration period and frequency were indicated with yellow arrows. The p values were detected by log-rank test. FIG. 7D Wright-Giemsa stained PB and BM, and H&E stained spleen and liver of the MLL-AF9-secondary leukemic mice treated with PBS control, miR-22 or miR-22 mutant nanoparticles.

FIG. 8A Comparison of effects of a set of miRNAs, which are down-regulated in AML, on MLL-AF9-induced colony forming. Colony-forming/replating assays (CFAs) were performed using mouse BM progenitor (lineage negative; Lin−) cells transduced with retrovirus of MSCV-neo+MSCV-PIG (Ctrl), MSCV-neo-MLL-AF9+MSCV-PIG (MLL-AF9), or MSCV-neo-MLL-AF9+MSCV-PIG-miR-150/miR-148a/miR-29a/miR-29b/miR-184/miR-342/miR-423/miR-22. FIG. 8B qPCR confirmation of the down-regulation of miR-22 in AML. Expression level of miR-22 in the mononuclear cells of 5 normal MNC control (NC), 42 AML (including 17 MLL-rearranged AML, 13 t(8;21), 5 t(15;17) and 7 inv(16)) and 20 MDS (including 17 (+8) and 3 (−7)) samples are shown. FIG. 8C Effects of miR-22 on the viability and apoptosis, FIG. 8D as well as growth of AML cells. MONOMAC-6 cells were transfected with MSCV-PIG (Ctrl), MSCV-PIG-miR-22 (miR-22), or miR-22 mutant (miR-22mut) plasmids. Cell viability and apoptosis were detected 48 hrs post-transfection. Cell growth was assessed by cell counts at a series of time points post-transfection. FIG. 8E Expression levels of miR-22 in various sub-populations of mouse normal hematopoietic cells. Expression levels of miR-22 in long-term HSC (LT-HSC; Lin−Sca1+c-Kit+Flk2−, LSKF−), short-term HSC (ST-HSC; Lin−Sca1+c-Kit+Flk2+, LSKF+), committed progenitor (CP; Lin−Sca1−c-Kit+), Gr-1+/Mac-1+ myeloid and B220+ lymphoid cells, were normalized to the level in lineage negative (Lin−) cells. Mean±SD values are shown. *, $p<0.05$. All the p values shown in this figure were generated by t-test.

FIG. 9A Overexpression level of miR-22 in bone marrow cells of MLL-AF9 and MLL-AF10-induced primary leukemic mice. 3~5 independent leukemic mice are included in each group. Mean±SD values are shown. *, $p<0.05$, t-test. FIG. 9B Flow cytometry analyses of the BM cells of both primary bone marrow transplantation (BMT) recipient mice, or FIG. 9C secondary BMT recipient mice. 0.5 million mouse BM cells collected at the end point were stained with APC-conjugated anti-mouse c-Kit or eFluor® 450-conjugated anti-mouse CD11b (Mac-1) antibodies. Proportions of c-Kit+ and/or Mac1+ cells are shown.

FIG. 10A Up-regulation of miR-22 level in MLL-ENL-ERtm cells after withdrawal of 4-OHT for 0, 7 or 10 days. FIG. 10B Down-regulation of CRTC1, FLT3 and MYCBP at the protein level by miR-22. MONOMAC-6 cells were transfected with MSCV-PIG-miR-22 (miR-22) or MSCV-PIG vector (Ctrl). Protein extractions of the cells were analyzed through Western-blotting assays 48 hrs post-transfection. FIG. 10C Down-regulation of Crtc1, Flt3, Mycbp, Bmi1, Cdk6 and Hmga1 by miR-22 overexpression. Protein levels in BM blast cells of leukemic mice transplanted with MLL-AF9 or MLL-AF9+miR-22 primary leukemic cells are shown. FIG. 10D miR-22 overexpression showed no significant influence on the level of MLL-fusion in MLL-AF9-leukemic mouse BM cells. Mouse BM progenitor cells bearing MLL-AF9 were retrovirally transduced with MSCV-PIG-miR-22 or MSCV-PIG vector. After 7 days' selection with puromycin, MLL levels were detected through qPCR. FIG. 10E Flow cytometry analyses of the BM cells of secondary BMT mice. 0.5 million mouse BM cells collected at the end point were stained with APC-conjugated anti-mouse c-Kit or eFluor® 450-conjugated anti-mouse CD11b (Mac-1) antibodies. Proportions of c-Kit+ and/or Mac1+ cells are shown. FIG. 10F Correlation between the expression levels of miR-22 and CDK6, HOXA7, RGS2, BMI1, FASN or HMGA1 in In-house_81S. The correlation coefficient (r) and p values were detected by "Pearson Correlation", and the correlation regression lines were drawn with the "linear regression" algorithm. FIG. 10G and FIG. 10I show that expression levels of the CREB downstream genes Cdk6, Hoxa7 and Rgs2, as well as the MYC downstream genes Bmi1, Fasn and Hmga1 were detected in the BM cells of the primary BMT recipient mice or FIG. 10H and FIG. 10J the secondary BMT recipients. The primary transplanted mice include MLL-AF9+Ctrl, MLL-AF9+miR-22, and MLL-AF9+miR-22 mutant (miR-22mut). The secondary recipients were transplanted with the blast cells of the primary MLL-AF9 mice retrovirally transduced with MSCVneo+MSCV-PIG (MA9-AML+Ctrl), MSCVneo-miR-22+MSCV-PIG (MA9-AML+miR-22), or MSCVneo-miR-22+MSCV-PIG-CRTC1/FLT3/MYCBP (MA9-AML+miR-22+CRTC1/FLT3/MYCBP). n=5 for each group. Mean±SD values of three replicates are shown. *, $p<0.05$. All the p values shown in this figure were generated by t-test, except for those shown in FIG. 10F that were generated by Pearson correlation test.

FIG. 11A DNA copy number of the miR-22 gene locus of 50 AML samples and 5 normal controls were tested. qPCR data were normalized against the chromosomal region of actin or FIG. 11B 6p22 probe. Mean values, standard deviations (error bars), and the 95% confidence internal (CI) are shown. FIG. 11C DNA copy-number loss of miR-22 in three independent AML datasets are shown. Dark blue: Homozygous deletion; Cyan: Heterozygous deletion.

FIG. 12A Expression levels of Tet1 and miR-22 in various sub-populations of mouse normal hematopoietic cells. Gene expression levels in long-term HSC (LT-HSC; Lin$^-$Sca1$^+$c-Kit$^+$Flk2$^-$, LSKF$^-$), committed progenitor (CP; Lin$^-$Sca1$^-$c-Kit$^+$) and Gr-1$^+$/Mac-1$^+$ myeloid cells, were normalized to the level in lineage negative (Lin$^-$) cells. FIG. 12B Expression of WDR81 in THP-1 cells 72 hours post-treatment with 1 μM ATRA or DMSO control. FIG. 12C Co-immunoprecipitation showing the binding between GFI1 and TET1 in HEK293T cells. FIG. 12D Effects of knockdown of TET1, EZH2 and/or SIN3A on GFI1 expression. FIG. 12E siRNA knockdown effects on TET1, EZH2 and SIN3A in THP-1 cells. Gene levels were detected 48 hrs post-transfection. FIG. 12F Effects of knockdown of TET1, EZH2 and/or SIN3A on WDR81 expression. The expression level of WDR81was detected in THP-1 cells 72 hours post-transfection with siRNAs targeting TET1, EZH2 and/or SIN3A. FIG. 12G Effects of knockdown of GFI1 on WDR81 expression. The expression level of WDR81 was detected in THP-1 cells transduced with lentiviral vectored GFI1 shRNA or control shRNA. FIG. 12H DNA methylation at miR-22 promoter region determined by bisulfite sequencing. Percentage of methylated CG (mCG %) at miR-22 promoter region in THP-1 cells treated with DMSO or 1 μM ATRA for 72 hrs were analyzed, with SLC43A2 (100 kbps downstream of miR-22 promoter) as a positive control of DNA methylation. FIG. 12I DNA methylation level at miR-22 promoter region of 194 AML patient samples from TCGA_194S is shown, with SLC43A2 as a positive control of DNA methylation. FIG. 12J Correlation analysis between miR-22 methylation and expression in 170 AML patient samples with both methylation and gene expression data from TCGA_194S. FIG. 12K qPCR analysis of miR-22 and TET1 expression in AML samples with DNA copy-number loss of miR-22. A total of 9 AML and 3 normal controls samples, all been studied in the analyses of Supplementary FIG. 4a/b, are included. The expression levels of miR-22 and TET1 are normalized to RNU48 and actin, respectively. The DNA copy numbers are normalized to those at the gene locus of actin. Mean±SD values are shown. *, p<0.05; **, p<0.01. All the p values shown in this figure were generated by t-test, except for the one shown in FIG. 12J that was generated by Pearson correlation test.

FIG. 13A $^1$H NMR spectra of G7 PAMAM dendrimer (upper panel) and G7-Cy5.5-NH$_2$ (lower panel). Characteristic dendrimer peaks are located between 2.0-3.5 ppm. Following conjugation, there is an appearance of new peaks between 7.0-8.5 ppm due to the aromatic protons on Cy5.5, corresponding to approximately 4 Cy5.5 per G7. FIG. 13B Formation of the G7-miR-22 dendriplex. G7 PAMAM dendrimers were labeled using the near infrared dye, Cy5.5 (red dots), and mixed with miR-22. Complex formation is driven by electrostatic forces between the cationic primary amine surface groups of the PAMAM dendrimer and the anionic phosphate backbone of miR-22. Schematic represents approximate theoretical mixing ratio and sizes of polyplex components. FIG. 13C Wright-Giemsa stained PB and BM, and H&E stained spleen and liver of the AE9a-secondary leukemic mice treated with PBS control, miR-22 or miR-22 mutant nanoparticles. FIG. 13D Expression levels of Crtc1, Flt3 and Mycbp in the BM cells of the PBS, miR-22- or miR-22 mutant-nanoparticle-treated secondary BMT recipient mice transplanted with MLL-AF9 primary leukemic blast cells. Mean±SD values are shown. *, p<0.05, t-test. FIG. 13E Wright-Giemsa stained PB and BM, and H&E stained spleen and liver of the non-transplanted NSGS control or MV4;11 xenotransplanted NSGS leukemic mice treated with PBS control, miR-22 or miR-22 mutant nanoparticles.

DETAILED DESCRIPTION

Figure 1A:
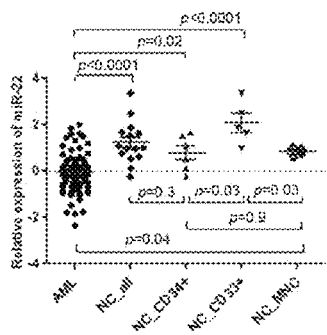
FIGS. 1A-1H demonstrate that miR-22 inhibits AML cell transformation and leukemogenesis.

The present disclosure is underpinned by discovery and investigation of a previously unappreciated TET1/GFI1/EZH2/SIN3A→miR-22→CREB-MYC signaling circuit, and insights into epigenetic/genetic mechanisms underlying the pathogenesis of AML that provide a basis for novel clinical methods and agents for treatment of AML based on up-regulating expression of or increasing presence of miR-22.

In contrast to the oncogenic role of miR-22 reported in myelodysplastic syndrome (MDS) and breast cancer, the present disclosure surprisingly establishes that miR-22 is an essential anti-tumor gatekeeper in de novo acute myeloid leukemia (AML) where it is significantly down-regulated. Forced expression of miR-22 is herein shown to significantly suppress leukemic cell viability and growth in vitro, and substantially inhibit leukemia development and maintenance in vivo. Mechanistically, miR-22 targets multiple oncogenes, including CRTC1, FLT3 and MYCBP, and thus represses the CREB and MYC pathways. The down-regulation of miR-22 in AML is caused by TET1/GFI1/EZH2/SIN3A-mediated epigenetic repression and/or DNA copy-number loss. Furthermore, administration of miR-22 via nanoparticle based delivery systems efficiently targets AML cells and significantly inhibits leukemia progression in vivo.

The mechanism of mediation of gene regulation in cancer by tet methylcytosine dioxygenase (TET) proteins remains unclear. The present disclosure establishes that in de novo acute myeloid leukemia (AML), TET1, but not TET2 (a reported direct target of miR-22 in myelodysplastic syndrome (MDS) and breast cancer[15, 16]) is implicated and TET1 inversely correlates with miR-22 in expression and negatively regulates miR-22 at the transcriptional level. Likely together with GFI1, TET1 recruits polycomb cofactors (e.g., EZH2/SIN3A) to the miR-22 promoter, leading to a significant increase in H3K27me3 occupancy and decrease in RNA pol II occupancy at that region, and thereby resulting in miR-22 repression in AML cells; such a repression can be abrogated by ATRA (all-trans-retinoic acid) treatment. Thus, the present disclosure provides a novel epigenetic regulation mechanism in leukemia involving the cooperation between TET1/GFI1 and polycomb factors.

Besides GFI1, it has been reported that LSD1 is also a binding partner of TET1[50]. Interestingly, LSD1 is known as a common binding partner shared by TET1 and GFI1, and mediates the effect of GFI1 on hematopoietic differentiation[51, 52]. Thus, it is possible that LSD1 might also participate in the transcriptional repression of miR-22 as a component of the GFI1/TET1 repression complex. The present investigators previously reported that TET1 cooperates with MLL-fusions in positively regulating their oncogenic co-targets in MLL-rearranged AML[14]. Here it is shown that TET1 can also function as a transcriptional repressor (of a miRNA) in cancer. The requirement of TET1-mediated regulation on expression of its positive (e.g., HOXA/MEIS1/PBX3)[14] or negative (e.g., miR-22) downstream effectors in leukemogenesis likely explains the rareness of TET1 mutations in AML[53], and highlights its potent oncogenic role in leukemia.

The aberrant activation of both CREB and MYC signaling pathways has previously been shown in AML[24, 25, 26, 54, 55], but the underlying molecular mechanisms remained elusive. Data set forth herein suggest that the activation of these two signaling pathways in AML can be attributed, at least in part, to the repression of miR-22, which in turn, results in the de-repression of CRTC1 (CREB pathway), FLT3 and MYCBP (MYC pathway), and leads to the up-regulation of oncogenic downstream targets (e.g., CDK6, HOXA7, BMI1, FASN and HMGA1) and down-regulation of tumor-suppressor downstream targets (e.g., RGS2).

Some embodiments are directed to a method of treating a patient suffering from acute myeloid leukemia (AML), the method comprising: administering to the patient at least one agent that upregulates expression of miR-22. All-trans-retonoic acid and NSC-370284 are known agents that either directly or indirectly increase expression of miR-22. According to specific embodiments, the patient suffers from de novo AML.

According to other embodiments, methods comprise administering miR-22. Generally, miRNAs are short (2-24 nt) non-coding RNAs that are involved in post-transcriptional regulation of gene expression in multicellular organisms by affecting both the stability and translation of mRNA. miRNAs are transcribed by RNA polymerase II as part of capped and polyadenylated primary transcripts (pre-miR-NAs) that can be either protein-coding or non-coding. The primary transcript is cleaved by the Drosha ribonuclease III enzyme to produce an approximately 70-nt stem precursor miRNA, which is further cleaved by the cytoplasmic Dicer ribonuclease to generate the mature miRNA and antisense miRNA* products. The mature miRNA is incorporated into a RNA-induced silencing complex, which recognizes target mRNAs through imperfect base pairing with the miRNA and most commonly results in translational inhibition or destabilization of the target mRNA. miR-22 is known to be ubiquitously expressed in various tissues, and the gene encoding miR-22 is located on the short arm of chromosome 17, in a minimal loss of heterozygosity region, thus being highly conserved across vertebrate species and suggesting functional significance. miR-22 has been previously identified as playing an important role in erythrocyte maturation. According to embodiments of the invention, miR-22 comprises According to some embodiments, miR-22 has 90% sequence homology to 5'-aagcugccaguugaagaacugu-3' (SEQ ID NO: 2), and in other more specific embodiments, miR-22 has 95% to SEQ ID NO: 2. In even more specific embodiments the miRNA consists essentially of SEQ ID NO: 2, wherein "consists essentially" permits inclusion of amino acids that are artifacts of production methods or modifications of the peptide for stability.

MiR-22 may be incorporated into a nanoparticle delivery system by complexing with, for example, a polymeric dendrimeric molecule. In very specific embodiments, the polymeric dendrimeric molecule comprises polyamidoamine (PAMAM) dendrimers, which are hyperbranched polymers having molecular uniformity, a narrow molecular weight distribution, defined size and shape, and a multifunctional "Velcro" surface. The polymers are nanoscale and comprise an ethyenediamine core, a repetitive branching amidoamine internal structure and a primary amine surface. Dendrimers grow off a central core in an iterative fabrication process, with each sub uent step representing a "generation" of dendrimer. Increasing generations, therefore, represent increasing molecular weight and a larger molecular diameter, with each new generation having twice the number of reactive sites at the surface and approximately double the molecular weight of the preceding generation. PAMAM dendrimers generally assume a sheroidal, globular shape at generation 4+. According to very specific embodiments, the nanoparticle complex comprises a G2, G3, G4, G5, G6, G7 or G8-PAMAM dendrimer. In more specific embodiments, the PAMAM dendrimer is G4-G8. In even more specific embodiments the PAMAM dendrimer is G7. Mixtures of generations are also contemplated.

According to some embodiments, the PAMAM dendromir is surface-functionalized with a ligand specific for an FLT3 receptor, said ligand comprising a natural and/or synthetic FLT3L peptide. Target AML cells have surface-localized FLT3 receptors. According to specific embodiments, the ligand specific for FLT3 receptor comprises a natural or synthetic FLT3L peptide. Functionally, the suitable synthetic FLT3L peptide must retain binding affinity for the FLT3 receptor. According to very specific embodiments, the synthetic FLT3L peptide is Flt3L peptide, although it will be readily perceived by a person of ordinary skill in the art that the surface peptide may be any FLT3L derivative that retains binding affinity for the target receptor. Human recombinant FLT3L proteins are available from ProSpec-Tany Technogene Ltd. (East Brunswick, N.J.), and a specific peptide comprises 155 amino acids of the extracellular domain of FLT3L (i.e., the soluble FLT3L form). A very specific synthetic Flt3L peptide containing 74 amino acids with the sequence of SSNFKVKFRELTDHLLKDYPVT-VAVNLQDEKHCKALWSLFLAQRWIEQLKTVAGSK MQTLLEDVNTEIHFVTSC (SEQ ID NO: 3) is available from Pierce Biotechnology, Inc. (Rockford, Ill.).

According to other specific embodiments, the ligand specific for FLT3 receptor comprises a synthetic FLT3L peptide having at least 50%, 60%, 70%, 80% or 90% sequence homology to SEQ ID NO: 3. In more specific embodiments, the ligand specific for FLT3 receptor comprises a synthetic FLT3L peptide having at least 90% sequence homology to SEQ ID NO: 3, and in even more specific embodiments, the synthetic FLT3L peptide essentially consists of SEQ ID NO: 3 (in this context, "essentially consists" means any amino acids present in addition to SEQ ID NO:3 arise from production processes or are other artifacts of synthetic processes including recombinant methods of production. MiR-22 may be modified in some aspects to increase stability. A non-limiting example of an miR-22 stability modification comprises 2'-O methylation. 2'-O-methylation is a common nucleoside modification of RNA wherein a methyl group is added to the 2' hydroxyl of the ribose moiety of a nucleoside, producing a methoxy group.

All experiments reported herein are conducted with a stability-modified 2'-OMe miR-22.

According to some embodiments, the miR-22 is modified for stability, and in very specific embodiments, the miR-22 stability modification comprises 2'-O methylation. In even more specific embodiments, the nanoparticle delivery system comprises G7-Flt3L-(2'OMe)miR-22.

In some embodiments, administering comprises systemically administering, such as by enteral or parenteral routes. Specific parenteral routes include, but are not limited to intravenous, intramuscular, subcutaneous, and inhaled. According to very specific embodiments, administering comprises intravenously administering. According to some embodiments, a therapeutic regime is provided comprising administering embodiments of miR-22 in conjunction with other therapies for AML.

According to other embodiments, formulations of miR-22, nanoparticle delivery systems comprising miR-22, and/or an agent, such as a small molecule that increases expression of miR-22, may be administered in conjunction with chemotherapeutic agents known as effective for the treatment of AML, for example, cytosine, arabinoside and anthracycline, or with small molecule inhibitors against MYC and/or CREB pathway effectors, to achieve optimal anti-leukemia effect with minimal side effects. In the alternative, nanoparticles comprising miR-22, or small molecule stimulators of endogenous expression of miR-22, may be administered as a secondary course of treatment after failure of a first course of treatment for AML. A non-limiting example of a small molecule known to increase expression of miR-22 is all-trans-retinoic acid (ATRA). Other non-limiting examples comprise coumarin and, in other specific embodiments, ultraviolet radiation may be administered to increase expression of miR-22.

Another embodiment is directed to a nanoparticle delivery system designed for sustained delivery of microRNA-22 (miR-22) to acute myeloid leukemia (AML) cells. The nanoparticle delivery system comprises polymeric dendrimers, such as poly(amidoamine) (PAMAM) dendrimers, complexed with miR-22. In very specific embodiments the at least one dendrimer is surface-functionalized with a ligand specific for FLT3 receptor. In specific embodiments the PAMAM dendrimers comprise between generation-2 and generation-8 dendrimers, and in more specific embodiments the PAMAM dendrimers comprises between generation 4 and generation-8 dendrimers. In very specific embodiments, the PAMAM dendrimers comprise generation 7 (G7) dendrimers.

Examples set forth below include proof-of-concept studies that demonstrate that the nanoparticles carrying miR-22 oligos significantly inhibit AML progression and prolong survival of leukemic mice in both bone marrow transplant (BMT) and xeno-transplantation models. Notably, miRNA-based nanoparticles have already entered clinical trials[56]. Overall, our results suggest that restoration of miR-22 expression/function (e.g., using miR-22-carrying nanoparticles or small-molecule compounds) holds great therapeutic potential to treat AML, especially those resistant to current therapies.

EXAMPLES

The following methodology applies generally or as indicated. Specific Examples follow. Examples are set forth to illustrate and support various aspects of the therapeutic methods and agents and should not be construed as limiting the full scope thereof, as defined by the appended claims.

AML and MDS Samples and Cell Lines

The AML and MDS patient samples were obtained at the time of diagnosis with informed consent at the University of Chicago Hospital (UCH), and were approved by the University of Chicago Hospital Institutional Review Board (UCHIRB). All patients were treated according to the protocols of the corresponding institutes/hospitals. THP-1, KOCL48, MV4;11, MEF and HEK293T cells were purchased from ATCC (Manassas, Va.) and maintained in the lab. The MLL-ENL-ER cell line was a gift from Dr. Robert Slany[31]. All the cell lines were tested for mycoplasma contamination yearly using a PCR Mycoplasma Test Kit (PromoKine).

Preparation of AML and MDS Samples

The primary AML and MDS samples were stored in liquid nitrogen until used. Blasts and mononuclear cells were purified by use of NycoPrep 1.077A (Axis-Shield, Oslo, Norway) according to the manufacturer's manual.

Human Normal Hematopoietic Control Cell Samples

The mononuclear cell (MNC) normal control samples were isolated from normal BM cells purchased from AllCells, LLC (Emeryville, Calif.) by use of NycoPrep 1.077A (Axis-Shield, Oslo, Norway) according to the manufacturer's manual.

Mouse Normal BM Cell Population Sorting

As described previously[23], wild-type C57BL6/J mice were used for the sorting. All laboratory mice were maintained in the animal facility at the University of Chicago and the University of Cincinnati. All experiments on mice in our research protocol were approved by Institutional Animal Care and Use Committee (IACUC) of the University of Chicago and the University of Cincinnati.

The long-term hematopoietic stem cells (LT-HSCs; Lin$^-$Sca1$^+$c-Kit$^+$Flk2$^-$, LSKF), short-term HSCs (ST-HSCs; Lin$^-$Sca1$^+$c-Kit$^+$Flk2$^+$, LSKF$^+$), and the committed progenitors (CP, Lin$^-$ Sca1$^-$c-Kit$^+$) were enriched by lineage$^+$ cell depletion (EasySep Mouse Hematopoietic Progenitor Cell Enrichment Kit; StemCell Technologies, Vancouver, BC), and purified by FACSAria flow cytometer (BD Biosciences, San Jose, Calif.) sorting after 20 μL/test fluorescein isothiocyanate-conjugated lineage (FITC-Lin) cocktail (including FITC-CD3 (17A2), FITC-B220 (RA3-6B2), FITC-CD11b (M1/70), FITC-TER-119 (TER-119), FITC-Gr1 (RB6-8C5)), 5 μg/mL phycoerythrin (PE)-Sca1 (D7), 1.5 μg/mL APC-c-Kit (ACK2) and 20 μg/mL PE-Cy5.5-Flk2 (A2F10) staining. Then, Gr1$^+$Mac1$^+$ myeloid cells and B220$^+$ B cells were sorted from BM cells after 2.5 μg/mL FITC-Gr1 (RB6-8C5), 2.5 μg/mL PE-Mac1 (M1/70) and 5 μg/mL APC-B220 (RA3-6B2) staining. All fluorescent antibodies used were purchased from eBioscience (San Diego, Calif.).

RNA Extraction and Quantitative RT-PCR

Total RNA was extracted with the miRNeasy extraction kit (Qiagen, Valencia, Calif.) and was used as template to synthesize cDNA for quantitative RT-PCR (qPCR) analysis in a 7900HT real-time PCR system (Applied Biosystems, Foster City, Calif.). TaqMan qPCR assay was performed to validate the differential expression patterns of miR-22 using commercial kits from Applied Biosystems (Cat. #4427975). Sequences for the controls are: sno202: 5'-GCTGTACTGACTTGATGAAAGTACTTTTGAACCCTTTTCCATCTGATG-3' (SEQ ID NO: 1); RNU6B: 5'-CGCAAGGATGACACGCAAATTCGTGAAGCGTTCCATATTTT-3' (SEQ ID NO: 4). qPCR with SYBR Green dye (Qiagen) was used to determine expression of mRNA genes. snoRNA202, RNU48, Gapdh or GAPDH were used as endogenous controls for qPCR of miRNA and mRNA, respectively. Each sample was run in triplicate. qPCR primers are available upon request. For determining the miR-22 DNA locus copy number, TaqMan qPCR assay was used as described previously[57].

Exiqon microRNA Microarray Assays and Affymetrix Exon Array Assays of Human Samples As described previously[17, 23], miRNA expression profiling assay of 85 (including 10 t(8;21), 9 inv(16), 9 t(15;17), 10 MLL-rearranged, 11 (+8), 29 normal karyotype, and 7 others) AML samples and 15 human normal BM samples was performed by Exiqon (Woburn, Mass.) using the miRCURY LNA™ arrays (v10.0; covering 757 human miRNAs). The 15 normal BM controls included six CD34+ hemtopoietic stem/progenitor, five CD33+ myeloid progenitor, and four MNC samples. In terms of patient samples, mononuclear (MNC) cells isolated from the BM or peripheral blood (PB) cells of the 85 AML patients were used. The expression values are log2 (Hy3/Hy5) ratios, which were obtained on the basis of the normalized data where replicated measurements on the same slide have been averaged. In addition, as described previously[14, 17, 23], a total of 100 human AML (including 30 t(8;21), 27 inv(16), 31 t(15;17) and 12 MLL-rearranged) and 9 normal BM samples (including 3 each of CD34$^+$ hematopoietic stem/progenitor, CD33$^+$ myeloid, and mononuclear cell (MNC) samples) were analyzed by use of Affymetrix GeneChip Human Exon 1.0 ST arrays (Affymetirx, Santa Clara, Calif.). The QC test and Affymetrix exon array assays were done in the core facility of National Human Genome Research Institute, NIH (Bethesda, Md.). Robust Multi-array Average (RMA)[58] was used for the data normalization with Partek Genomics Suite (Partek Inc., St. Louis, Mich.). The complete microarray data set has been deposited in the GEO database under the accession codes GSE34184 and GSE30285.

Amongst the above 100 human AML samples, 81 samples (i.e., the In-house_81S; including 29 t(8;21), 26 inv(16), and 26 t(15;17) AML) have been also included in the Exiqon microRNA array assay[21]. The microarray dataset of those 81 AML samples has been deposited in GEO database under the accession code GSE27370.

Affymetrix Gene Arrays of Mouse Samples

As described previously[17], a total of 15 mouse BM samples including 6 primary (including 3 each of negative control and MLL-AF9) and 9 secondary (including 3 negative control and 6 MLL-AF9) obtained from the in vivo mouse BM reconstitution assays were analyzed by use of Affymetrix GeneChip Mouse Gene 1.0 ST Array (Affymetrix, Santa Clara, Calif.). The RNA quality control, cDNA amplification, hybridization, and image scan were conducted in the Functional Genomics Facility of University of Chicago. RMA[58] was used for the data normalization with Partek Genomics Suite (Partek Inc., St. Louis, Mich.). The microarray dataset of those 15 mouse AML samples has been deposited at GEO database (GSE34185).

Affymetrix Microarray Assay of GSE37642_562S Set

The GSE37642_562S set (n=562) AML samples (including 30 t(8;21), 38 inv(16), 24 t(15;17), 38 MLL-rearranged, 6 del(5q), 16 del(7q), 15 inv3/t(3/3), 74 complex, 199 normal karyotype, and 122 others) were analyzed by use of Affymetrix Human Genome U133Plus2.0 GeneChips (n=140) or Affymetrix Human Genome U133A and B (U133A+B; n=422) GeneChips. RMA method[58] was used for data normalization. The AML samples were collected by the German AMLCG study group. Part of the microarray data have been reported previously[44]. The GEO ID of the entire data set is GSE37642.

TCGA Data Sets

The Cancer Genome Atlas (TCGA) AML database[22] includes mRNA gene expression profiling data of 183 adult de novo AML cases (i.e., TCGA_183S; including 7 t(8;21), 11 inv(16), 17 t(15;17), 9 MLL-rearranged, 3 t(9;22), 22 complex, 78 normal karyotype, and 36 others), which were generated by use of Affymetrix Human Genome U133Plus2.0 GeneChips. Among the 183 AML cases, 177 (including 7 t(8;21), 11 inv(16), 16 t(15;17), 9 MLL-rearranged, 3 t(9;22), 22 complex, 75 normal karyotype, and 34 others) also have microRNA expression profiles as detected by IlluminaGA_miRNASeq platform, and the mRNA/miRNA profile data of the 177 AML cases were collectively referred to as TCGA_177S. 194 adult de novo AML cases (including 7 t(8;21), 11 inv(16), 15 t(15;17), 9 MLL-rearranged, 3 t(9;22), 24 complex, 91 normal karyotype, and 34 others) with DNA methylation data as detected by Infinium HumanMethylation450 BeadChip were referred to as TCGA_194S. The mRNA/miRNA expression data and methylation data were downloaded from https://tcga-data.nci.nih.gov/tcga/dataAccessMatrix.htm?mode=ApplyFilter&showMatrix=true&diseaseType=LAML&tumorNormal=TN&tumorNormal=T&tumorNormal=NT.

Cell Culture and Transfection

These experiments were conducted as described previously[17, 23] with some modifications.

THP-1, KOCL-48 and MV4;11 cells were grown in RPMI medium 1640 (Invitrogen, Carlsbad, Calif.) containing 10% FBS, 1% HEPES and 1% penicillin-streptomycin. MONO-MAC-6 cells were maintained in RPMI 1640 supplemented with 10% FBS, 1% HEPES, 2 mM L-Glutamine, 100×Non-Essential Amino Acid, 1 mM sodium pyruvate, 9 μg/ml insulin and 1% penicillin-streptomycin. Plasmids or siRNAs were transfected into MONOMAC-6 cells with Cell Line Nucleofector Kit V following program T-037, and THP-1 and KOCL-48 cells following program U-001, using the Amaxa® Nucleofector® Technology (Amaxa Biosystems, Berlin, Germany). Experiments were performed 48 hours after transfection.

For the ATRA-treatment study, THP-1 cells were seeded at a concentration of 0.4×10$^6$/mL and treated with ATRA (1 μmol/L) or vehicle control (DMSO, 0.001%) for 72 hours before cells were collected for RNA analysis or CUP assays.

The MLL-ENL-ERtm cell line was kept in RPMI 1640 supplemented with interleukin 3 (IL-3), IL-6, and granulocyte-macrophage colony-stimulating factor (GM-CSF), 10 ng/ml; SCF 100 ng/ml; 10% FBS and 1% penicillin-streptomycin. 4-Hydroxy-tamoxifen (4-OHT) (Sigma-Aldrich, St. Louis, Mo.) was added at a 100 nM final concentration as a 1 mM stock solution in ethanol. Cells were collected for experiments at the indicated days after drug withdrawal.

The MEF and HEK293T cells were kept in DMEM (Invitrogen, Carlsbad, Calif.) containing 10% FBS, 1% HEPES and 1% penicillin-streptomycin; HEK293T cells were transfected with Qiagen Effectene Transcription Kit (Qiagen, Valencia, Calif.) following the manufacturer's protocol. All the cell lines were mycoplasma negative.

Lentivirus Production, Precipitation and Infection

All the plasmid for packaging lentivirus, including pMD2.G, pMDLg/pRRE and pRSV-Rev, were purchased from Addgene (Cambridge, Mass.). Firstly, 0.5 μg pMD2.G, 0.3 μg pMDLg/pRRE, 0.7 μg pRSV-Rev and 1.5 μg shRNA constructs, i.e. shGFI1 and control (purchased from GE Dharmacon, Pittsburgh, Pa.) were co-transfected into HEK-293T cells in 60 mm cell culture dish with Effectene Transfection Reagent (QIAGEN, Valencia, Calif.). The lentivirus particles were harvested at 48 and 72 hours after transfection and concentrated with PEG-it™ Virus Precipitation Solution (SBI). Finally, the lentivirus particles were directly added into leukemic cells and these cells were washed with PBS 24-48 hours after infection.

Cell Apoptosis, Viability and Proliferation Assays

These experiments were conducted as described previously[17, 23] with some modifications. For apoptosis and viability assays, 48 hours after transfection, cells were collected and seeded with requested concentration. Cell apoptosis and viability were assessed using ApoLive-Glo Multiplex Assay Kit (Promega, Madison, Wis.) following the corresponding manufacturer's manuals. For cell proliferation assays, per million cells were electroporated with 1.5 µg plasmid. 24 hours after transfection, cells were seeded in 96-well plates at the concentration of 10,000 cells/well. Cell numbers were counted at the indicating days.

Plasmid Construction

The home-prepared expression vector of miR-22, i.e. MSCV-PIG-miR-22, was amplified by PCR using primers: forward: 5'-GCC CTC GAG TCT AGA CTC CAG TTC-3' (SEQ ID NO: 5) and reverse: 5'-GGG GAA TTC CTA CTC CTC AAT CCA G-3' (SEQ ID NO: 6), and was subsequently cloned into the XhoI and EcoRI sites of the retrovirus vector MSCV-PIG (i.e., MSCV-puro-IRES-GFP vector; bearing GFP gene), a kind gift from Drs. Gregory Hannon, Scott Hammond, and Lin He (Cold Spring Harbor Laboratory, Cold Spring Harbor, N.Y.). The other miR-22 construct, the MSCV-PIG-miR-22_2 expression vector, was a gift from Dr. Pier P. Pandolfi (Harvard Medical School, Boston, Mass.)[59]. The MSCVneo-MLL-AF9 plasmid[60] was kindly provided by Dr. Scott Armstrong (Harvard Medical School, Boston, Mass.). The MSCV-FLT3-CDS plasmid[61] was a gift from Dr. Michael Cleary (Stanford University, Stanford, Calif.). The p1005-Crtc1 plasmid was provided by Dr. Sheena Josselyn (The Hospital for Sick Children, Toronto, Canada)[62], and sub-cloned into MSCV-PIG vector. The MSCV-PIG-MYCBP plasmid was PCR-amplified using primers: forward 5'-AAA CTC GAG ATG GCC CAT TAC AAA GC-3' (SEQ ID NO: 7) and reverse 5'-CCG GAA TTC CTA TTC AGC ACG C-3' (SEQ ID NO: 8). The 3'UTR constructs of CRTC1 and FLT3 containing putative binding sites for miR-22 were amplified by PCR from human normal bone marrow mononuclear cells using the primers below: CRTC1-3'UTR: forward 5'-GCC ATT ACT AGT CCC ACC TGA GTG-3'(SEQ ID NO: 9) and reverse 5'- GCC ATT AAG CTT GAG GAC AGA AGC-3'(SEQ ID NO: 10); FLT3-3'UTR: forward 5'-GCC GCC ACT AGT AGG AAC AAT TTA GTT TTA AGG-3' (SEQ ID NO: 11) and reverse 5'-CGC AAG CTT GTG GGG ACA AGA GTA ACT TTA-3'(SEQ ID NO: 12), and then cloned into pMIR-REPORT™ Luciferase miRNA Expression Reporter Vector (Ambion, Austin, Tex.). Site mutations were induced by PCR based on the sequence shown previously for the miR-22 binding site(s) mutant of 3'UTR of CRTC1 and FLT3. The miR-22 promoter region (−1,100/+55 bp, as was identified by Bar et al.[45]) was PCR amplified using primers: forward 5'-AAT AAT GAG CTC AAG GTC GGA CG-3' (SEQ ID NO: 13) and reverse 5'-AAT AAT GAT ATC CTT TAG CTG GGT C-3'(SEQ ID NO: 14), and cloned into the SacI and EcoRV sites of the pGL4.15 Luciferase Reporter Vector (Promega, Madison, Wis.). The MSCV-Tet1 construct was as described previously[14]. All the above insertions were confirmed by DNA sequencing.

Chromatin Immunoprecipitation (ChIP)

ChIP assay was performed, as described previously[14, 17], with SABiosciences Corporation's ChampionChIP™ One-Day kit (Qiagen, Frederick, Md.) following the manufacturer's protocol, with some modifications. Briefly, pellets of 5×10$^6$ cells were treated with fresh fixing buffer (1% formaldehyde) for 10 min at 37° C. to crosslink DNA and proteins. The reaction was terminated by the addition of stop buffer and incubated at room temperature for 5 min. After cell lysis, the cross-linked chromatin was sonicated to an average size of ~500 bp and was immunoprecipitated with antibodies against TET1, GFI1 (Santa Cruz Biotechnology Inc., Santa Cruz, Calif.), the N'-terminal portion of MLL (MLL-N), the C'-terminal of MLL (MLL-C), H3K27Me3, H3K4Me3, RNA polymerase II, EZH2, SIN3A or IgG (Abcam, Cambridge, Mass.). Purified ChIP DNA was amplified by real-time qPCR using specific primers targeting the CpG-enriched upstream region of human miR-22: Forward: 5'-GTT GTT GGA GTC GTG AGT G-3' (SEQ ID NO: 15); reverse: 5'-CGC TCC ACC TTT CCT TAA A-3' (SEQ ID NO: 16); or mouse miR-22: Forward: 5'-TGA ATG GGC GGG AGT AA-3' (SEQ ID NO: 17); reverse: 5'-CCAC GAG CTG CGA ATG AA-3' (SEQ ID NO: 18).

Bisulfite Sequencing

THP-1 cells were treated with 1µM ATRA or DMSO control for 72 hours. Genomic DNA was extracted thereafter. 1µg of genomic DNA was then applied to MethylCode Bisulfite Conversion Kit (Invitrogen, Carlsbad, Calif.) following the manufacturers' instructions. After bisulfite conversion, 3µl of purified converted DNA was PCR amplified using ZymoTaq DNA polymerase (Zymo Research, Irvine, Calif.) following the manufacturers' instructions. The PCR products were purified using PCR purification kits (Qiagen, Valencia, Calif.) and sent for sequencing. Primers applied in the PCR assays: miR-22 promoter: forward: 5'- TTT GTT TAT TTT TGT TTT TTG GTT-3' (SEQ ID NO: 19); reverse: 5'-ACA ACC CCT CCT TAT TAA AAT C-3' (SEQ ID NO: 20); SLC43A2: forward: 5'-TGT TTT GTT TTT ATG GAG TGA TTT G-3' (SEQ ID NO: 21); reverse: 5'-AAA AAT AAC CAT AAA CCA TCC TTC C-3'(SEQ ID NO: 22).

Luciferase Reporter and Mutagenesis Assays

Luciferase reporter and mutagenesis assays were conducted as described previously[17, 23], with some modifications. Briefly, for transfection, HEK293T cells were plated in 96-well plates at a concentration of 6,000 cells/well in triplicate for each condition. For the miR-22 targeting CRTC1 and FLT3 experiments, after overnight incubation, cells were transfected with 20 ng of the pMIR-REPORT bearing the CRTC1 or FLT3 3'UTR or the 3'UTRs with miR-22 binding site mutations, and 20 ng of MSCV-miR-22 or an empty MSCV vector using Effectene Transfection Reagent (Qiagen, Valencia, Calif.) according to the manufacturer's protocol. pMIR-REPORT™ Beta-galactosidase Reporter Control Vector (Ambion, Austin, Tex.) (1 ng) was cotransfected for transfection efficiency control in all transfections. Cells were lysed and firefly luciferase and β-galactosidase activities were detected using Dual-Light® Combined Reporter Gene Assay System (Applied Biosystems, Foster City, Calif.) 48 hrs post-transfection. Firefly luciferase activity was normalized to β-galactosidase activity for each transfected well. For the Tet1 targeting miR-22 study, HEK293T cells were transfected with 20 ng MSCV-Tet1 construct and/or 20 ng pGL4.15-miR-22 promoter. The succeeding luciferase reporter assay was conducted according to the manufacture's protocol (Promega, Madison, Wis.). Each experiment was performed in triplicate and repeated three times.

Co-immunoprecipitation Analysis

For immunoprecipitation, cells were washed with ice-cold PBS and lysed in 800 µl Nonidet P-40 solubilization buffer (50 mM Hepes, pH 8.0, 250 mM NaCl, 0.5% Nonidet P-40, 10% glycerol, 2 mM EDTA, 1 mM NaF, plus 10 µg/ml aprotinin, 10 µg/ml benzamidine, and 0.2 mM PMSF). The following procedures are performed as described previously[63]. GFI1 was precipitated by using protein A Sepharose beads coated with 400 ng rabbit anti-GFI1 antibody (Santa Cruz Biotechnology Inc., Santa Cruz, Calif.). Lysates and immunoprecipitation complexes were separated and detected by Western blotting.

Packaging of Recombinant Retroviruses and CFA Assays

These experiments were conducted as described previously[17, 23] with some modifications. Briefly, retrovirus vectors were co-transfected with pCL-Eco packaging vector (IMGENEX, San Diego, Calif.) into HEK293T cells using Effectene Transfection Reagent (Qiagen, Valencia, Calif.) to produce the retroviruses. BM cells were harvested from a cohort of 4- to 6-week-old B6.SJL (CD45.1) donor mice after five days of 5-fluorouracil (5-FU) treatment, and primitive hematopoietic progenitor cells were enriched with Mouse Lineage Cell Depletion Kit (Miltenyi Biotec Inc., Auburn, Calif.). An aliquot of enriched hematopoietic progenitor cells were added to retroviral supernatant together with polybrene in a conical tube, which were centrifuged at 2,000 g for 2 hours at 32° C. (i.e., "spinoculation"[14, 17, 23]) and then the media was replaced with fresh media and incubated for 20 hrs at 37° C. Next day, the same procedure was repeated once.

On the day following the second spinoculation, an equivalent of $2.0 \times 10^4$ cells were plated into a 35 mm Petri dish in 1.5 ml of Methocult M3230 methylcellulose medium (Stem Cell Technologies Inc, Vancouver, Canada) containing 10 ng/ml each of murine recombinant IL-3, IL-6, and granulocyte-macrophage colony-stimulating factor (GM-CSF), and 30 ng/ml of murine recombinant SCF (R&D Systems, Minneapolis, Minn.), along with 1.0 mg/ml of G418 and/or 2 µg/ml of puromycin. For each transduction, there were two duplicate dishes. Cultures were incubated at 37° C. in a humidified atmosphere of 5% $CO_2$ in air. The colonies were replated every 7 days under the same conditions. The colony-forming/replating assays were repeated 3 times.

Primary and Secondary Bone Marrow Transplantation (BMT)

These experiments were conducted as described previously[14, 17, 23] with some modifications. For primary BMT assays shown in FIG. 1E, normal bone marrow cells of B6.SJL (CD45.1) mice were retrovirally transduced with MSCV-neo+MSCV-PIG (as control; Ctrl), MSCV-neo+MSCV-PIG-miR-22 (i.e., miR-22), MSCV-neo-MLL-AF9+MSCV-PIG (i.e., MA9), MSCV-neo-MLL-AF9+MSCV-PIG-miR-22 (i.e., MA9+miR-22), or MSCV-neo-MLL-AF9+MSCV-PIG-miR-22 mutant (i.e., MA9+miR-22mut), through two rounds of spinoculation. Then, retrovirally transduced cells were plated into methylcellulose medium supplied with a set of cytokines to form colonies as described in the CFA assays. Seven days later, colony cells were collected and washed, and then were injected by tail vein into lethally irradiated (960 rads) 8- to 10-week-old C57BL/6 (CD45.2) recipient mice with $1.5 \times 10^5$ donor cells plus a radioprotective dose of whole BM cells ($1 \times 10^6$; freshly harvested from a C57BL/6 mouse) per recipient mouse. Notably, as the colony cells were under selection of both G418 (1.0 mg/ml) and puromycin (2 µg/ml) for a week, all donor cells (i.e., the collected colony cells) must be positive for retroviral transductions of both MSCVneo- and MSCV-PIG-based constructs. Thus, MLL-AF9 and miR-22 (or miR-22mut) must be ectopically co-expressed in MA9+miR-22 (or MA9+miR-22mut) donor cells, which actually were confirmed by qPCR. Indeed, due to the potent inhibitory effect of miR-22 on MLL-AF9-induced colony forming, we had to prepare more mouse BM progenitor cells for the co-transduction of MLL-AF9 and miR-22. Thus, they were plated them in a larger number of dishes than what we did for other groups of co-transductions. After BMT, all recipient mice were watched for leukemogenesis for a period of over 200 days or till the end point that the mice developed full-blown AML or other sever illness. For primary BMT assays shown in FIG. 1G, C57BL/6 mouse (CD45.2) BM progenitor cells were co-transduced with MSCVneo-MLL-AF10, together with MSCV-PIG-miR-22 or MSCV-PIG vector. Cells were grown in RPMI medium 1640 (Invitrogen, Carlsbad, Calif.) containing 10% FBS, 1% HEPES and 1% penicillin-streptomycin, supplemented with a supply of stem cell factor (SCF), IL-3 and IL-8. The cells were selected with both puromycin and G418 for 7 days before transplantation. After that, $1.5 \times 10^5$ donor cells plus a radioprotective dose of whole bone marrow cells ($1 \times 10^6$; freshly harvested from a B6.SJL (CD45.1) mouse) were injected into per lethally irradiated (960 rads) 8- to 10-week-old B6.SJL recipient mouse.

Figure 1B:
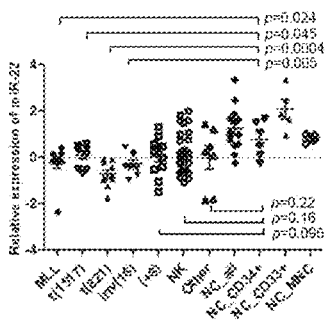
Figure 1C:
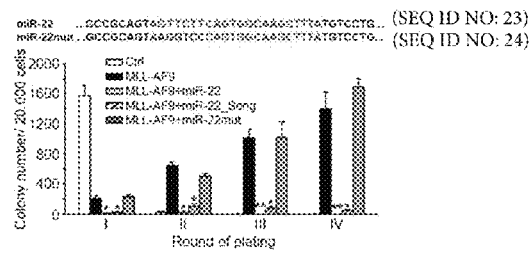
Figure 1D:
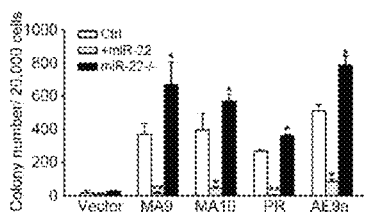
Figure 1E:
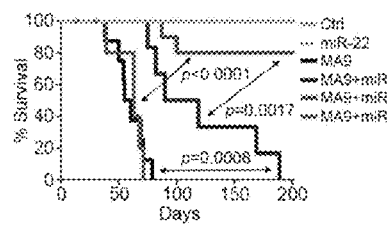
Figure 1F:
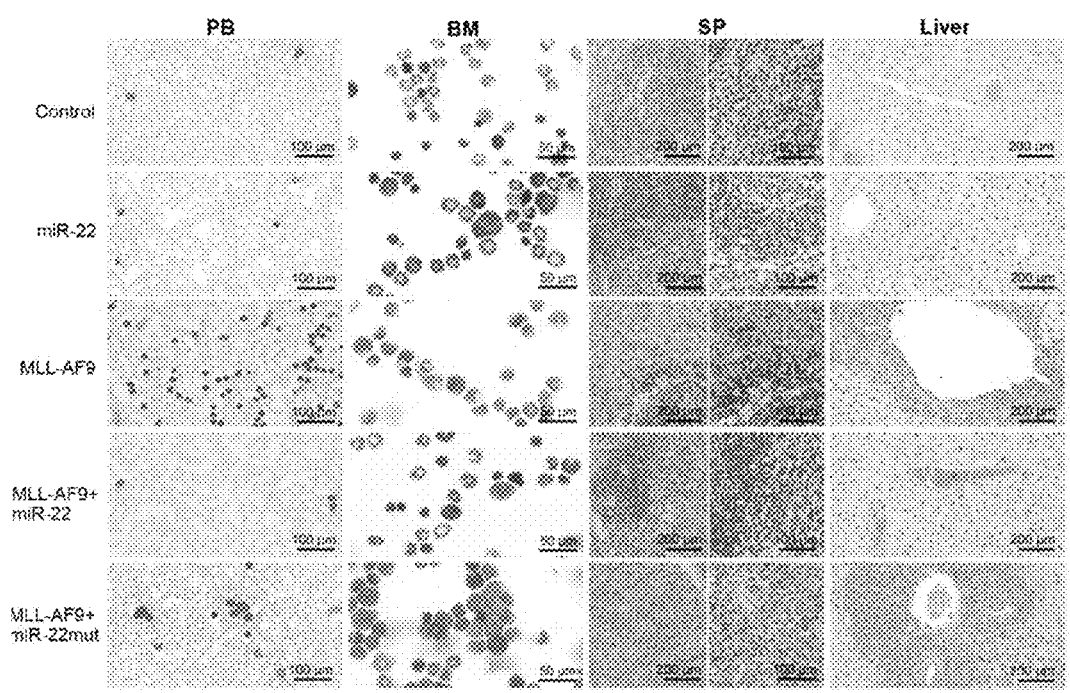
Figure 1G:
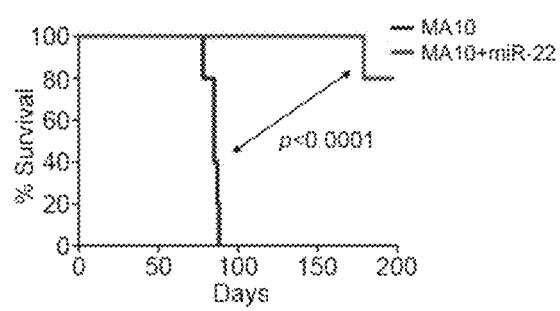
Figure 1H:
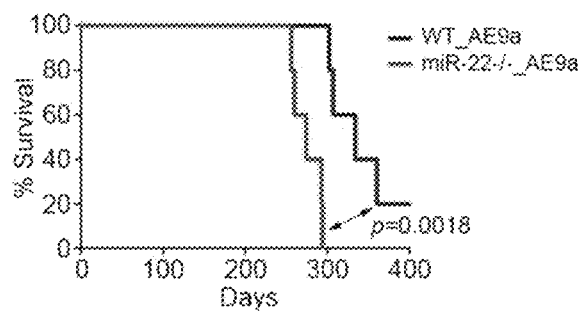

For primary BMT assays shown in FIG. 1H, C57BL/6 mouse (CD45.2) BM progenitor cells or miR-22$^{-/-}$ BM progenitor cells were retrovirally transduced with MSCV-PIG-AE9a. The cells were selected with puromycin for 7 days before transplantation. After that, $1.5 \times 10^5$ donor cells plus a radioprotective dose of whole bone marrow cells ($1 \times 10^6$; freshly harvested from a B6.SJL (CD45.1) mouse) were injected into per lethally irradiated (960 rads) 8- to 10-week-old B6.SJL recipient mouse.

Figure 2A:
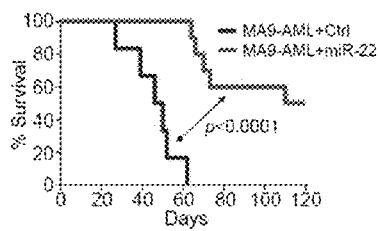
FIGS. 2A-2D show the effect of miR-22 on the maintenance of AML in vivo.
Figure 2B:
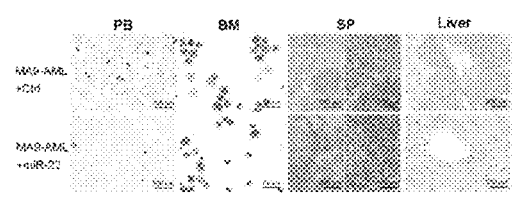
Figure 2C:
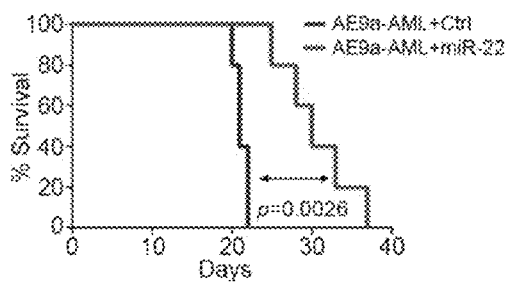
Figure 2D:
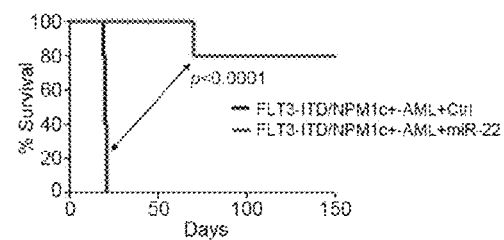

For secondary BMT assay shown in FIGS. 2A, 2C and 2D, leukemic BM cells isolated from the primary leukemic mice bearing MLL-AF9, AML9-ET9a (AE9a) or FLT3-ITD/NPM1c$^+$ were retrovirally transduced with MSCV-PIG+MSCVneo (as control; MA9-AML+Ctrl, AE9a-AML+Ctrl, or FLT3-ITD/NPM1c$^+$-AML+Ctrl) or MSCV-PIG+MSCVneo-miR-22 (i.e., MA9-AML+miR-22, AE9a-AML+miR-22, or FLT3-ITD/NPM1c$^+$-AML+miR-22). Similarly, retrovirally transduced cells were plated into methylcellulose medium supplied with puromycin and G418 (for selection) and a set of cytokines to form colonies. Seven days later, the colony cells were collected and washed, and then were transplanted into sub-lethally irradiated (480 rads) 8- to 10-week-old C57BL/6 (CD45.2) secondary recipient mice via tail vein injection, with the dosage of $1.5 \times 10^5$ donor cells per recipient mouse.

Figure 4A:
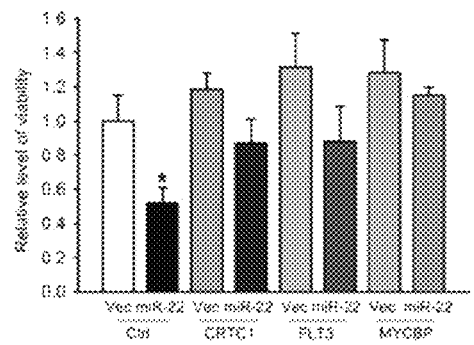
FIG. 4A Relative viability and apoptosis FIG. 4B levels of MONOMAC-6 cells transfected with MSCV-PIG-CRTC1, -FLT3 or -MYCBP alone, or together with MSCVneo-miR-22. Values were detected 48 hours post-transfection.
Figure 4B:
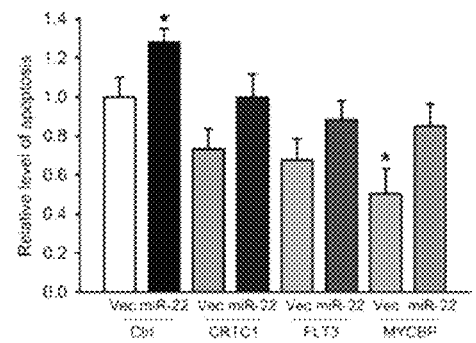
FIG. 4C Rescue effects of CRTC1, FIG. 4D FLT3, and FIG. 4E MYCBP on the inhibition of MONOMAC-6 growth mediated by miR-22. Cells counts at the indicated time points are shown. Mean±SD values are shown. *, p<0.05, t-test.
FIG. 4F In vivo rescue effects of CRTC1, FLT3 and MYCBP on the inhibition of MLL-AF9-induced leukemogenesis mediated by miR-22. The secondary recipients were transplanted with BM blast cells of the primary MLL-AF9 leukemic mice retrovirally transduced with MSCVneo+MSCV-PIG (MA9-AML+Ctrl; n=7), MSCVneo-miR-22+MSCV-PIG (MA9-AML+miR-22; n=10), MSCVneo-miR-22+MSCV-PIG-CRTC1 (MA9-AML+miR-22+CRTC1; n=5), MSCVneo-miR-22+MSCV-PIG-FLT3 (MA9-AML+miR-22+FLT3; n=6), or MSCVneo-miR-22+MSCV-PIG-MYCBP (MA9-AML+miR-22+MYCBP; n=6). Kaplan-Meier curves for all the five groups of transplanted mice are shown. MA9-AML+Ctrl vs. MA9-AML+miR-22, p<0.001 (log-rank test); MA9-AML+Ctrl vs. any other groups, p>0.05 (log-rank test).
FIG. 4G Wright-Giemsa stained PB and BM, and H&E stained spleen and liver of the secondary leukemic mice.
Figure 4C:
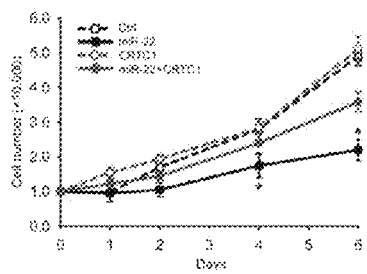
Figure 4D:
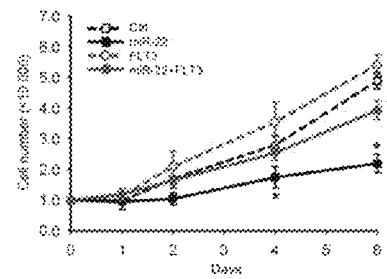
Figure 4E:
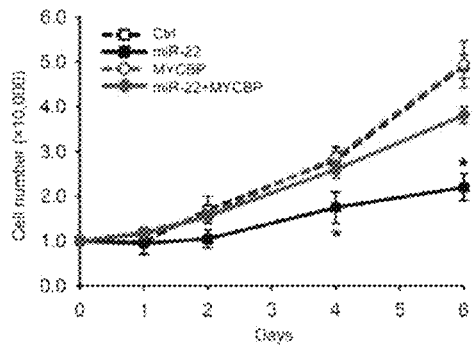
Figure 4F:
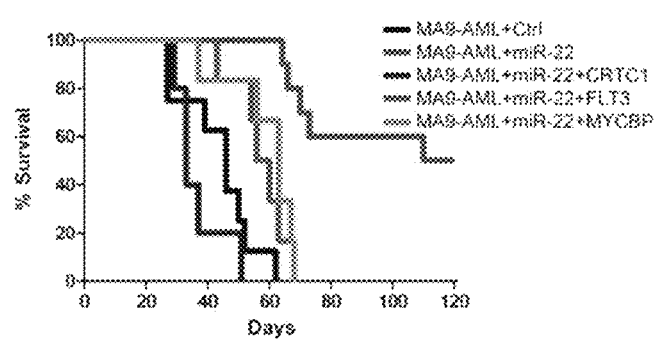

For secondary BMT assays shown in FIG. 4F, leukemic BM cells isolated from the primary leukemic mice bearing MLL-AF9 fusion were retrovirally transduced with MSCV-neo+MSCV-PIG (i.e., MA9-AML+Ctrl), MSCV-neo-miR-22+ MSCV-PIG (i.e., MA9-AML+miR-22), MSCV-neo-miR-22+MSCV-PIG-CRTC1 (i.e., MA9-AML+miR-22+CRTC1), MSCV-neo-miR-22+MSCV-PIG-FLT3 (i.e., MA9-AML+miR-22+FLT3), or MSCV-neo-miR-22+MSCV-PIG-MYCBP (i.e., MA9-AML+miR-22+MYCBP). Again, retrovirally transduced cells were plated into methylcellulose medium supplied with G418 and puromycin (for selection) as well as a set of cytokines to form colonies. Seven days later, the colony cells were collected and washed, and then were transplanted into sub-lethally irradiated (480 rads) 8- to 10-week-old C57BL/6 (CD45.2) secondary recipient mice via tail vein injection, with the dosage of $1.5 \times 10^5$ donor cells per recipient mouse.

Preparation of Cy5.5 Labelled G7 PAMAM Dendrimers

G7 PAMAM dendrimers obtained from Sigma-Aldrich (St. Louis, Mo.) were purified and fluorescently labelled using an N-hydroxysuccinimide ester of cyanine5.5 (NHS-Cy5.5) (Lumiprobe Corporation, Hallandale Beach, Fla.), as has been previously reported[64]. In brief, G7 PAMAM dendrimers (38.7 mg, 332 nmol) were dissolved in 2 ml ddH$_2$O, to which NHS-Cy5.5 (3.75 mg, 3.32 μmol) in 400 μl DMSO was added dropwise, and the reaction allowed to proceed under vigorous stirring for 24 h at room temperature. Excess NHS-Cy5.5 was removed using an Amicon Ultra-15 Centrifugal Filter Unit (MWCO 10000, Millipore, Billerica, Mass.) at 4000 rpm and 4° C. for 20 min and washing with ddH$_2$O ten times. Remaining product was re-dissolved in ddH$_2$O and lyophilized, resulting in G7-Cy5.5-NH$_2$. All products were characterized by $^1$H NMR using a 400 MHz Bruker DPX-400 spectrometer (Bruker BioSpin Corp., Billerica, Mass.).

Nanoparticle Treatment in BMT or Xeno-transplantation Models

Figure 7A:
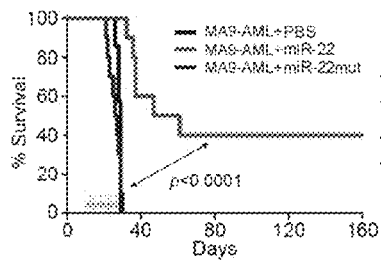
FIG. 7A-FIG. 7D demonstrate the therapeutic effect of miR-22-nanoparticles in treating AML.
Figure 7B:
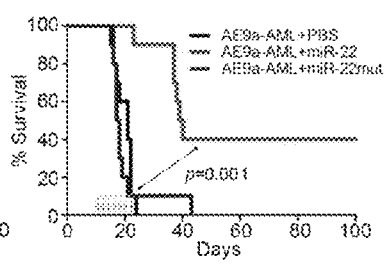

For secondary BMT followed with G7-Cy5.5-NH$_2$ dendrimer treatment shown in FIGS. 7A and 7B, leukemic BM cells isolated from the primary leukemic mice (CD45.1) bearing MLL-AF9 or AE9a fusion were transplanted into sub-lethally irradiated (480 rads) 8- to 10-week-old C57BL/6 (CD45.2) secondary recipient mice via tail vein injection, with the dosage of 1.5×10$^5$ donor cells per recipient mouse. After the onset of leukemia (when mice had an engraftment (CD45.1) over 20% and/or white blood cell counts higher than 4×10$^9$/L; for the MLL-AF9 and AE9a secondary transplantation models, usually 10 days post transplantation), the recipient mice were injected with PBS control, or 0.5 mg/kg miR-22 or miR-22 mutant RNA oligos formulated with G7-NH2-nanoparticles, i.v., every other day, until the PBS-treated group all died of leukemia.

Figure 7C:
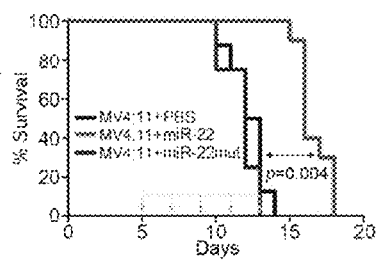

For xeno-transplantation followed with G7-Cy5.5-NH2 dendrimer treatment shown in FIG. 7C, MV4;11 cells were transplanted into NSGS (NSG-SGM3) mice via tail vein injection, with the dosage of 5×10$^5$ donor cells per recipient mouse. Five days after xeno-BMT, the recipient mice were injected with PBS control, or 0.5 mg/kg miR-22 or miR-22 mutant RNA oligos formulated with G7-NH2-nanoparticles, i.v., every other day, until the PBS-treated mice all died of leukemia.

The Maintenance, Monitoring, and End-point Treatment of Mice

C57BL/6 (CD45.2), B6.SJL (CD45.1) mice were purchased from the Jackson Lab (Bar Harbor, Me., USA) or Harlan Laboratories, Inc (Indianapolis, Ind., USA). NSGS (NSG-SGM3) immunodeficient mice[49] and miR-22$^{-/-}$ [20] mice were purchased from the Jackson Lab (Bar Harbor, Me., USA) and were bred and maintained in house. Both male and female mice were used for the experiments. All laboratory mice were maintained in the animal facility at the University of Chicago and the University of Cincinnati. All experiments on mice in our research protocol were approved by Institutional Animal Care and Use Committee (IACUC) of the University of Chicago and the University of Cincinnati. The maintenance, monitoring, and end-point treatment of mice were conducted as described previously[14, 17, 23].

Western Blotting

Western blotting was conducted as described previously[14, 17, 23] with some modifications. Briefly, transiently transfected MONOMAC-6 cells were harvested and lysed with RIPA buffer (Thermo Scientific, BufferRockford, Ill.). Proteins from the lysate were fractionated by electrophoresis through 4-15% polyacrylamide gels (BIO-RAD, Hercules, Calif.) and transferred to polyvinylidene fluoride membranes using Tris-Glycine Transfer buffer (Thermo Scientific). Blots were incubated with IRDye 800CW-conjugated or 700CW-conjugated antibody and infrared fluorescence images were obtained with the Odyssey infrared imaging system (Li-Cor Bioscience, Lincoln, Nebr.). 100-200 ng/mL anti-CRTC1, anti-FLT3, anti-MYCBP, anti-BMI1, anti-CDK6, anti-PGK1 (Santa Cruz Biotechnology Inc., Santa Cruz, Calif.), anti-HMGA1 (Abcam, Cambridge, Mass.) and anti-GAPDH (Thermo Scientific) antibodies were used to detect corresponding proteins.

Target Gene Prediction

Putative targets of miR-22 was predicted by TragetScan (http://www.targetscan.org)[18].

DNA Copy-number Analysis of miR-22 Gene Locus in Human AML

The copy number data of AML from The Cancer Genome Atlas (TCGA) project were downloaded from Broad Firehose's analyses runs. The putative copy number calls were determined using GISTIC 2.0[65]. The latest GISTIC analyses data were obtained using the following shell command: "firehose_get-o "GISTIC" analyses latest LAML".

The .cel files of affymetrix SNP 6.0 data for GSE21107[66] and GSE23452[67] were downloaded from NCBI GEO. The raw data were preprocessed using PennCNV[68]. Then ASCAT[69] was used to obtain the copy number alterations. The putative copy number calls were determined using GISTIC 2.0 as described above.

Software and Statistical Analyses

The miRNA and gene/exon array data analyses, as well as qPCR data analyses were conducted by use of Partek Genomics Suite (Partek Inc, St. Louis, Mich.), TIGR Mutiple Array Viewer software package (TMeV version 4.6; TIGR, Rockville, Mass.)[70], and/or Bioconductor R packages. The miRNA-gene expression correlation was analyzed by use of Partek Genomics Suite (Partek Inc, St. Louis, Mich.). The t-test, Kaplan-Meier method, and log-rank test, etc. were performed with WinSTAT (R. Fitch Software), GraphPad Prism version 5.00 (GraphPad Software, San Diego, Calif.), and/or Partek Genomics Suite (Partek Inc, St. Louis, Mich.). The p-values less than 0.05 were considered as statistically significant. Significance analysis of microarrays (SAM) (Tusher et al., 2001), embedded in the TMeV package (TIGR, Rockville, Mass.), was used to identify the genes that are significantly (q<0.05; false discovery rate, FDR<0.05) dysregulated in the MLL-AF9-mediated mouse leukemia samples or human AML samples relative to the normal controls. Pearson correlation was used in the analysis of the correlation between miR-22 and candidate genes in expression. The list of transcription factors that have evolutionarily conserved binding sites within the miR-22 promoter region (i.e., the adjacent upstream CpG island) was obtained by searching UCSC Genome Browser (https://genome.ucsc.edu/cgi-bin/hgTracks?db=hg19&position=chr17%3A1614689-1623188&hgsid=467686877_3vyTlry3a40ZiT7dfAaAIAsYA2R6).

Example 1

The Down-regulation of miR-22 in De Novo AML

Figure 8A:
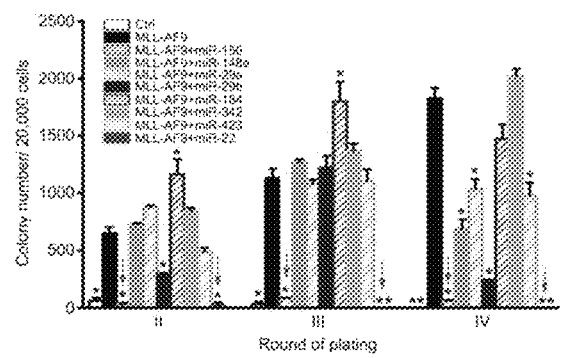
FIG. 8A-FIG. 8E demonstrates that miR-22, which is down-regulated in AML, inhibits AML cell transformation and growth.
Figure 8B:
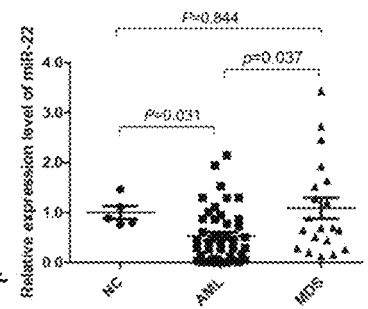

Through Exiqon miRNA array profiling, a set of miRNAs, such as miR-150, miR-148a, miR-29a, miR-29b, miR-184, miR-342, miR-423 and miR-22, were previously identified by the present investigators as being significantly down-regulated in AML compared to normal controls[17]. Here it was shown that amongst all the above miRNAs, miR-150 and especially miR-22 exhibited the most significant and consistent inhibitory effect on MLL-AF9-induced cell immortalization in colony-forming/replating assays (CFA) (FIG. 8A). In contrast to the reported up-regulation of miR-22 in MDS[16], the original microarray data[17] (FIGS. 1A and 1B) and new qPCR independent validation data (FIG.

8B) demonstrated a significant and global down-regulation of miR-22 in de novo AML relative to normal controls. Notably, miR-22 is significantly down-regulated in AML samples (p<0.05) compared to all three sub-populations of normal control cells, i.e., normal CD34+ hematopoietic stem/progenitor cells (HSPCs), CD33+ myeloid progenitor cells, or mononuclear cells (MNCs) (see FIG. 1A). Expression of miR-22 is significantly down-regulated in all or the majority of individual subsets of AML samples than in the normal CD33+ or CD34+ cell samples (FIG. 1B).

Figure 8C:
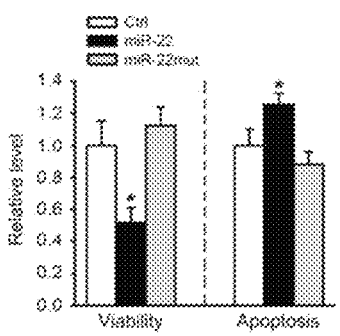
Figure 8D:
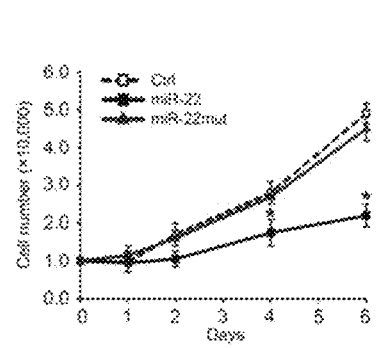
Figure 8E:
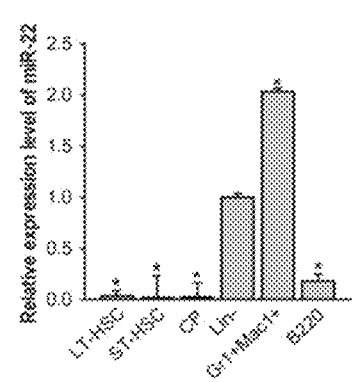

To rule out the possibility that the inhibitory effect of miR-22 shown in FIG. 8A was due to a non-specific effect of our miR-22 construct, we included the MSCV-PIG-miR-22 construct from Song et al.[16] in a repeated CFA. Both miR-22 constructs dramatically inhibited MLL-AF9-induced colony formation (FIG. 8A). As the "seed" sequences at the 5' end of individual miRNAs are essential for the miRNA-target binding[18], we also mutated the 6-bases "seed" sequence of miR-22 and found that the miR-22 mutant did not inhibit colony formation anymore (FIG. 8C). In human AML cells, forced expression of miR-22, but not miR-22 mutant, significantly inhibited cell viability and growth/proliferation, while promoting apoptosis (FIG. 8C and FIG. 8D).

Furthermore, as miR-22 is globally down-regulated in all major types of AML (FIG. 1B), we also investigated the role of miR-22 in colony formation induced by other oncogenic fusion genes, including MLL-AF10/t(10;11), PML-RARA/t(15;17), and AML1-ETO9a/t(8;21)[19]. As expected, forced expression of miR-22 significantly inhibited colony formation induced by all individual oncogenic fusions; conversely, miR-22 knockout[20] significantly enhanced colony forming (FIG. 1D). These results suggest that miR-22 likely plays a broad anti-tumor role in AML.

In accordance with the potential anti-tumor function of miR-22 in AML, miR-22 was expressed at a significantly higher level (p<0.05) in human normal CD33+ myeloid progenitor cells than in more immature CD34+ HSPCs or MNC cells (a mixed population containing both primitive progenitors and committed cells) (see FIG. 1A and 1B), implying that miR-22 is up-regulated during normal myelopoiesis. Similarly, we showed that miR-22 was also expressed at a significantly higher level in mouse normal bone marrow (BM) myeloid (Gr-1+/Mac-1+) cells, relative to lineage negative (Lin−) progenitor cells, long-term hematopoietic stem cells (LT-HSCs), short-term HSCs (ST-HSCs), and committed progenitors (CPs) (FIG. 1E), further suggesting that miR-22 is up-regulated in normal myelopoiesis.

Example 2

The Anti-tumor Effect of miR-22 in the Pathogenesis of AML

Figure 9A:
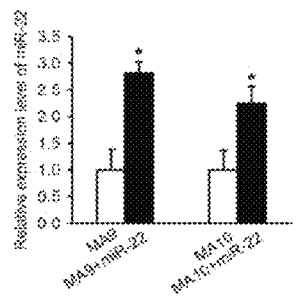
FIG. 9A-FIG. 9C sets forth results of investigations of the role of miR-22 in AML in vivo.
Figure 9B:
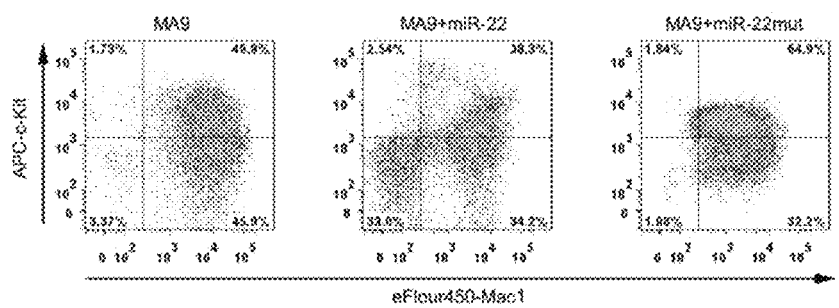

Through bone marrow transplantation (BMT) assays, we showed that forced expression of miR-22 (but not miR-22 mutant) dramatically blocked MLL-AF9 (MA9)-mediated leukemogenesis in primary BMT recipient mice, with a more potent inhibitory effect than miR-150 (FIG. 1E; FIG. 9A). All MA9+miR-22 mice exhibited normal morphologies in peripheral blood (PB), BM, spleen and liver tissues (FIG. 1F), with a substantially reduced c-Kit+ blast cell population in BM (FIG. 9B). Forced expression of miR-22 also almost completely inhibited leukemogenesis induced by MLL-AF10 (FIG. 1G, FIG. 9A). Conversely, miR-22 knockout significantly promoted AML1-ETO9a (AE9a)-induced AML (FIG. 1H). Thus, the repression of miR-22 is critical for the development of primary AML. Notably, forced expression of miR-22 in MLL-AF9 and MLL-AF 10 leukemia mouse models caused only a 2-3 fold increase in miR-22 expression level (FIG. 9A), in a degree comparable to the difference in miR-22 expression levels between human AML samples and normal controls (FIG. 1A), suggesting that a 2-3 fold change in miR-22 expression level appears to be able to exert significant physiological or pathological effects.

Figure 9C:
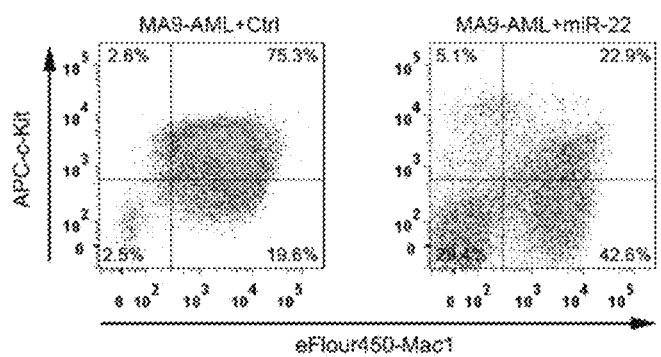

To examine whether the maintenance of AML is also dependent on the repression of miR-22, we performed secondary BMT assays. Forced expression of miR-22 remarkably inhibited progression of MLL-AF9-, AE9a-, or FLT3-ITD/NPM1c+-induced AML in secondary recipient mice (FIGS. 2A-2D), resulting in largely normal morphologies in PB, BM, spleen and liver tissues (FIG. 2B and FIG. 9C). Collectively, our findings demonstrate that miR-22 is a pivotal anti-tumor gatekeeper in both development and maintenance of various AML.

Example 3

Identification of Critical Target Genes of miR-22 in AML

To identify potential targets of miR-22 in AML, a series of data analyses was performed. Analysis of In-house_81S[21] and TCGA_177S[22] datasets revealed a total of 999 genes exhibiting significant inverse correlations with miR-22 in expression. Of them, 137 genes, including 21 potential targets of miR-22 as predicted by TargetScan[18] (Table 1), were significantly up-regulated in both human and mouse AML compared to normal controls as detected in two additional in-house datasets[14, 23]. Amongst the 21 potential targets, CRTC1, ETV6, and FLT3 are known oncogenes[24, 25, 26, 27, 28, 29] ENREF 3. We then focused on these three genes, along with MYCBP that encodes the MYC binding protein and is an experimentally validated target of miR-22[30] although due to technical issue it was not shown in the 21 gene list (Table 1), for further studies.

TABLE 1

List of the 22 candidate target genes of miR-22 in AML

| Gene | In-house_81S (Pearson correlation analysis of candidate targets and miR-22 in expression) | | TCGA_177S (Pearson correlation analysis of candidate targets and miR-22 in expression) | | 15-mouse-sample set (9 MLL-AF9 AML vs. 6 normal control samples; SAM) | | 109-human-sample set (100 AML vs. 9 normal control samples; SAM) | |
|---|---|---|---|---|---|---|---|---|
| | r | p | r | p | Fold change | q-value | Fold change | q-value |
| ANKRD28 | −0.43 | 0.0001 | −0.34 | <0.0001 | 1.72 | <0.0001 | 1.67 | 0.0015 |
| ANKRD52 | −0.22 | 0.0458 | −0.17 | 0.0199 | 1.22 | <0.0001 | 1.13 | 0.0348 |
| B3GNTL1 | −0.41 | 0.0001 | −0.49 | <0.0001 | 1.28 | <0.0001 | 1.34 | 0.0107 |
| CDK6 | −0.27 | 0.0139 | −0.34 | <0.0001 | 2.38 | <0.0001 | 1.15 | 0.0131 |
| CRTC1 | −0.31 | 0.0045 | −0.16 | 0.0359 | 1.32 | <0.0001 | 1.18 | 0.0173 |
| DDX51 | −0.36 | 0.0010 | −0.30 | 0.0001 | 1.65 | <0.0001 | 1.18 | 0.0112 |
| DFFB | −0.26 | 0.0185 | −0.19 | 0.0103 | 1.35 | <0.0001 | 1.19 | 0.0213 |
| ETV6 | −0.31 | 0.0042 | −0.40 | <0.0001 | 1.70 | <0.0001 | 1.53 | 0.0044 |
| FLT3 | −0.21 | 0.0307 | −0.35 | <0.0001 | 4.48 | <0.0001 | 2.12 | 0.0028 |
| MBD3 | −0.28 | 0.0126 | −0.21 | 0.0048 | 1.31 | <0.0001 | 1.15 | 0.0238 |
| METTL10 | −0.30 | 0.0066 | −0.20 | 0.0075 | 1.21 | 0.0053 | 1.32 | 0.0091 |
| MFSD10 | −0.46 | <0.0001 | −0.28 | 0.0002 | 1.60 | <0.0001 | 1.61 | 0.0036 |
| MTL5 | −0.29 | 0.0081 | −0.29 | 0.0001 | 1.50 | <0.0001 | 1.17 | 0.0407 |
| MYCBP | NA | NA | −0.15 | 0.0481 | 1.11 | 0.034 | NA | NA |
| OLA1 | −0.31 | 0.0048 | −0.35 | <0.0001 | 1.37 | <0.0001 | 1.10 | 0.0446 |
| RCC2 | −0.24 | 0.0323 | −0.23 | 0.0026 | 1.37 | 0.0002 | 1.33 | 0.0041 |
| SGTA | −0.34 | 0.0019 | −0.20 | 0.0082 | 1.13 | 0.0014 | 1.53 | <0.0001 |
| SPATS2 | −0.33 | 0.0024 | −0.30 | 0.0001 | 1.05 | 0.052 | 1.21 | 0.0152 |
| TRIM13 | −0.23 | 0.0392 | −0.31 | <0.0001 | 2.58 | <0.0001 | 1.46 | 0.0016 |
| TRIM46 | −0.23 | 0.0387 | −0.26 | 0.0006 | 1.25 | <0.0001 | 1.27 | 0.0054 |
| ZCCHC3 | −0.26 | 0.0187 | −0.28 | 0.0001 | 1.63 | 0.0002 | 1.13 | 0.026 |
| ZNF512B | −0.39 | 0.0003 | −0.42 | <0.0001 | 2.03 | <0.0001 | 1.38 | 0.0019 |

Note:
r, correlation coefficient;
p, p-value;
NA, not available.
SAM, significant analysis of microarrays[1].
Notably, MYCBP was not included in Affymetrix GeneChip ® Human Exon ST Arrays and thus it was absent in our in-house human AML datasets[2,3]; as a result, MYCBP was not shown in the original 21 candidate target gene list, although MYCBP exhibited a significant inverse correlation in expression with miR-22 in the TCGA dataset and was significantly up-regulated in the mouse AML dataset.

Figure 3A:
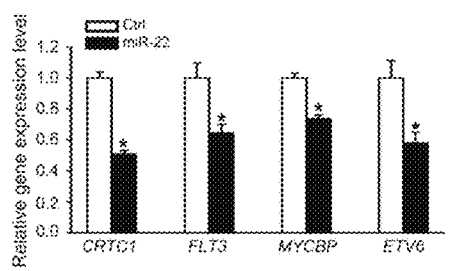
Figure 3B:
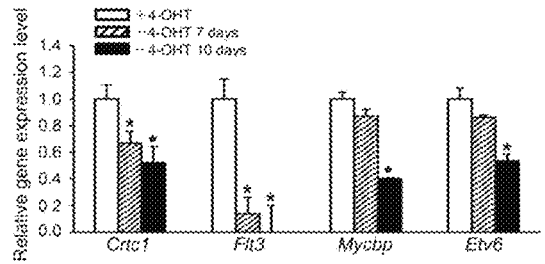
Figure 3C:
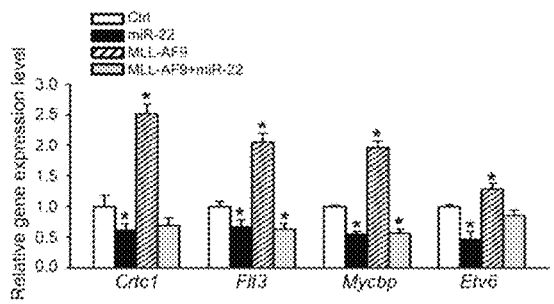
Figure 3D:
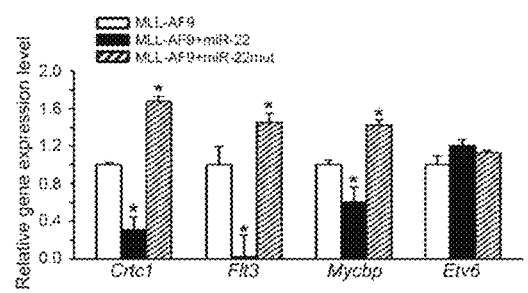
Figure 3E:
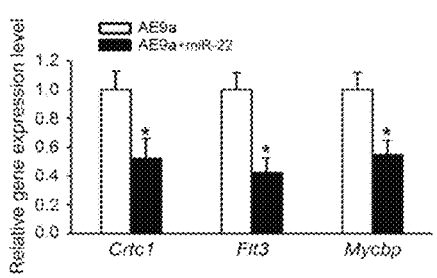
Figure 3F:
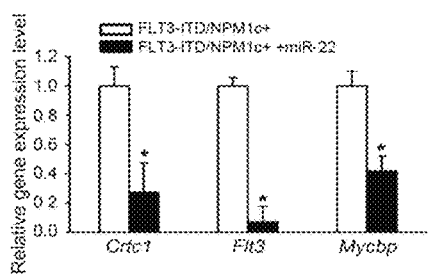
Figure 10A:
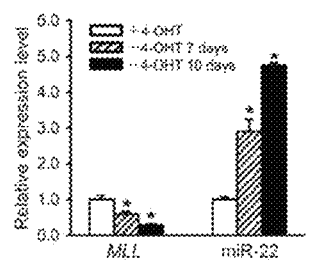
FIG. 10A-FIG. 10J demonstrate repression of the CREB and MYC pathways by miR-22.
Figure 10B:
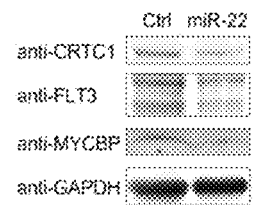
Figure 10C:
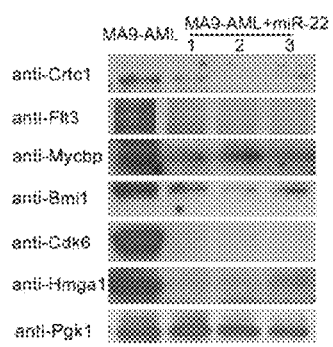
Figure 10D:
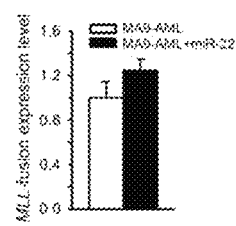

As expected, all four genes were significantly down-regulated in expression by ectopic expression of miR-22 in human MONOMAC-6/t(9;11) cells (FIG. 3A). The coincidence of down-regulation of those genes and up-regulation of miR-22 was also observed in mouse MLL-ENL-ERtm cells, a leukemic cell line with an inducible MLL-ENL derivative[31], when MLL-ENL was depleted by 4-hydroxytamoxifen (4-OHT) withdrawal (FIG. 3B and FIG. 10A). While MLL-AF9 remarkably promoted expression of those four genes in mouse BM progenitor cells, co-expressed miR-22 reversed the up-regulation (FIG. 3C). In leukemia BM blast cells of mice with MLL-AF9-induced AML, the expression of Crtc1, Flt3 and Mycbp, but not Etv6, was significantly down-regulated by co-expressed miR-22 (but not by miR-22 mutant) (FIG. 3D). Because miR-22-mediated down-regulation of Etv6 could be observed only in the in vitro models (FIG. 3A-FIG. 3C) but not in the in vivo model (FIG. 3D), which probably due to the difference between in vitro and in vivo microenvironments, we decided to focus on the three target genes (i.e., Crtc1, Flt3 and Mycbp) that showed consistent patterns between in vitro and in vivo for further studies. The repression of Crtc1, Flt3 and Mycbp was also found in leukemia BM cells of mice with AE9a or FLT3-ITD/NPM1c+-induced AML (FIGS. 3E and 3F). As Mycbp is already a known target of miR-22[30], here we further confirmed that FLT3 and CRTC1 are also direct targets of miR-22 (FIGS. 3G and 3H). The down-regulation of CRTC1, FLT3 and MYCBP by miR-22 at the protein level was confirmed in both human and mouse leukemic cells (FIGS. 10B and 10C). Overexpression of miR-22 had no significant influence on the level of leukemia fusion genes (FIG. 10D).

Figure 4G:
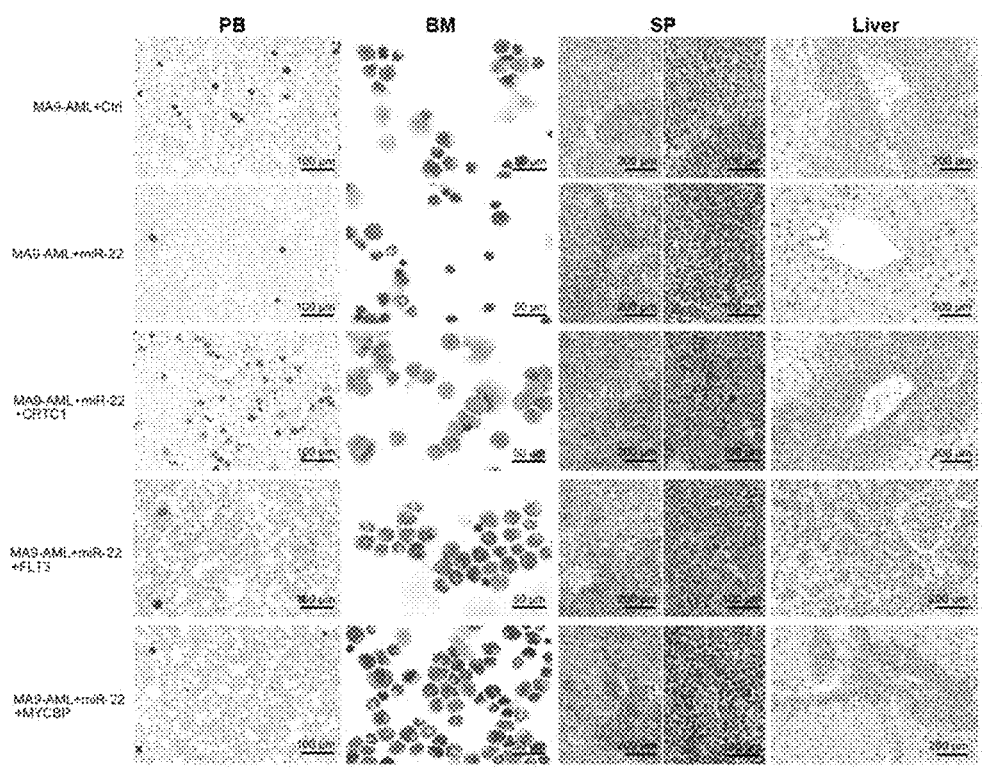
Figure 10E:
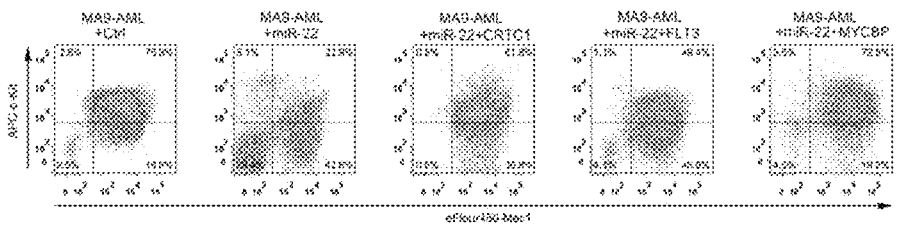

Co-expression of the coding region (CDS) of each of the three target genes (i.e., CRTC1, FLT3 and MYCBP) largely reversed the effects of miR-22 on cell viability, apoptosis and proliferation (FIGS. 4A-4E). More importantly, in vivo BMT assays showed that co-expressing CRTC1, FLT3 or MYCBP largely rescued the inhibitory effect of miR-22 on leukemogenesis (FIG. 4F, FIG. 4G, and FIG. 10E). Our data thus suggest that CRTC1, FLT3 and MYCBP are functionally important targets of miR-22 in AML.

Example 4 miR-22 Represses Both CREB and MYC Signaling Pathways

Figure 10F:
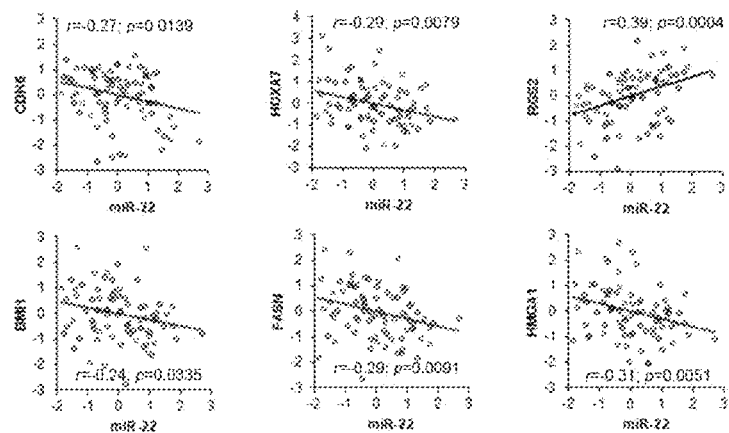
Figure 10G:
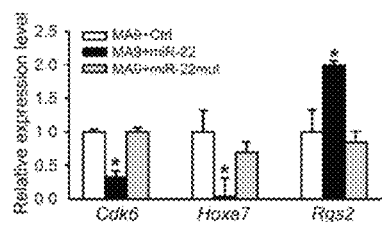
Figure 10H:
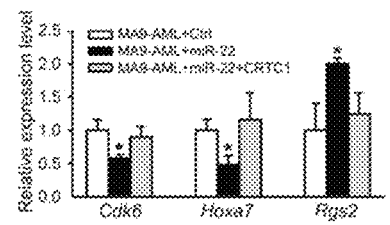

CRTC1, a CREB regulated transcription coactivator, facilitates CREB in regulating transcription of its targets, in both normal and malignant hematopoiesis[24, 25, 26] ENREF 39. CDK6, HOXA7 and RGS2 are known direct targets of CREB that are either positively (CDK6 and HOXA7) or negatively (RGS2) regulated by CREB[32, 33, 34, 35] ENREF 32. In both In-house_81S[21] and TCGA_177S[22] datasets, CDK6 and HOXA7 inversely, while RGS2 positively, correlated with miR-22 in expression (Table 2; FIG. 10F). In leukemic BM blast cells from primary and secondary BMT recipients, overexpression of miR-22 (but not miR-22 mutant) significantly down-regulated expression of Cdk6 and Hoxa7, while up-regulating Rgs2, which could be reversed by co-expressing CRTC1 (FIG. 10G and FIG. 10H). These results suggest that miR-22 represses the CREB signaling pathway in AML by targeting CRTC1.

Figure 10I:
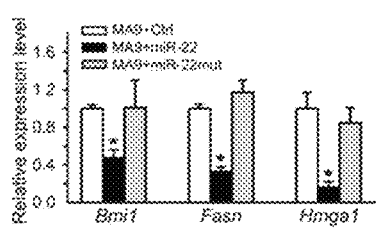
Figure 10J:
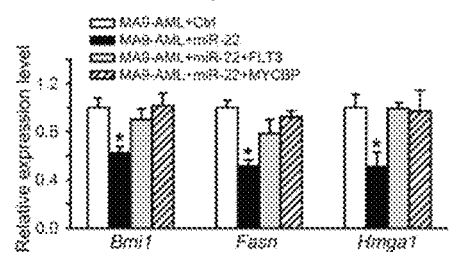

MYCBP, a MYC binding protein, is essential for MYC-mediated gene regulation[30]. FLT3 is an upstream regulator of MYC[17]. In leukemic BM cells, forced expression of miR-22, but not miR-22 mutant, significantly repressed expression of MYC downstream oncogenic targets Bmi1, Fasn and Hmga1[36, 37, 38]; the repression could be reversed by co-expressing MYCBP or FLT3 (FIGS. 10I and 10J). Those three genes all showed significant inverse correlations with miR-22 in expression in human AML (Table 2; FIG. 10F). The miR-22-induced repression of Bmi1, Cdk6 and Hmga1 at the protein level was also observed (FIG. 10C).

TABLE 2

List of functionally important downstream target genes of the CREB or MYC signaling pathways that exhibit a significant inverse correlation of expression with miR-22 in AML

| Signaling Pathway | Gene | In-house_81S (Pearson correlation analysis of candidate genes and miR-22 in expression) | | TCGA_177S (Pearson correlation analysis of canddiate genes and miR-22 in expression) | |
|---|---|---|---|---|---|
| | | r | p | r | p |
| CREB | CDK6 | −0.27 | 0.0139 | −0.34 | <0.0001 |
| | HOXA7 | −0.29 | 0.0079 | −0.16 | 0.0345 |
| | RGS2 | 0.39 | 0.0004 | 0.50 | <0.0001 |
| MYC | BMI1 | −0.24 | 0.0335 | −0.12 | 0.0455 |
| | FASN | −0.29 | 0.0091 | −0.26 | 0.0004 |
| | HMGA1 | −0.31 | 0.0051 | −0.18 | 0.0145 |

Note:
r, correlation coefficient; p, p-value.

Example 5

DNA Copy-number Loss of miR-22 Gene Locus in AML

Figure 11A:
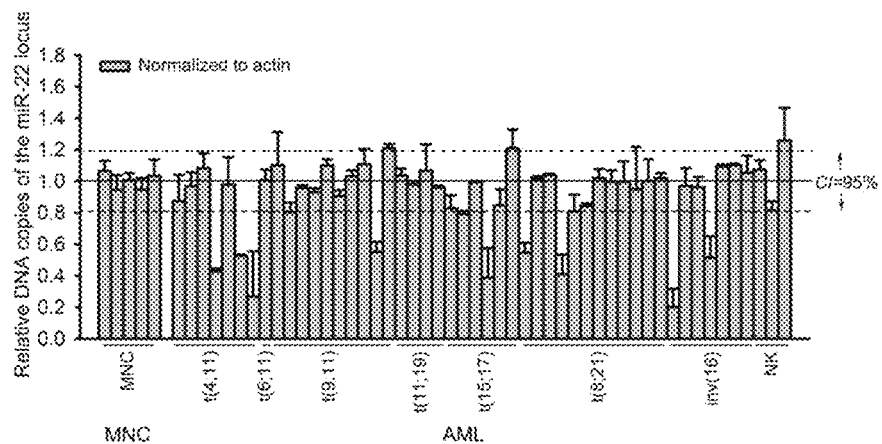
FIG. 11A-FIG. 11C demonstrate DNA copy-number loss of the miR-22 gene locus in AML.
Figure 11B:
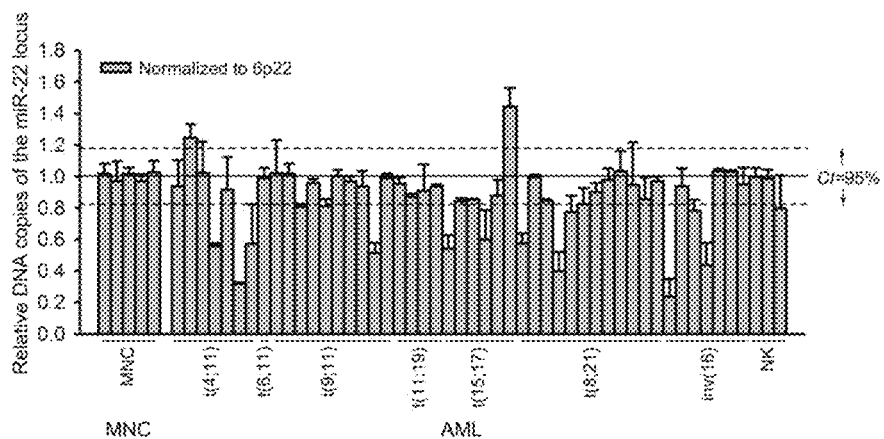
Figure 11C:

DNA copy-number loss of tumor-suppressor gene(s) is a hallmark of many cancers including AML[39]. Deletions of human chromosome 17 band p13.3, where miR-22 is located, have been frequently reported in various types of leukemia, lymphoma and solid tumors[40, 41, 42, 43]. Here we found that 18% (9/50) of the AML samples showed deletions (mostly hemizygous) of the miR-22 gene locus (FIGS. 11A and 11B). Similarly, in analysis of three publically available AML datasets, we found that 7%~9% of the AML cases carried loss of one or even two alleles of the miR-22 locus (FIG. 11C). Therefore, DNA copy-number loss in miR-22 gene locus does exist in AML cases.

Example 6

Expression of miR-22 is Epigenetically Repressed in AML

Figure 5A:
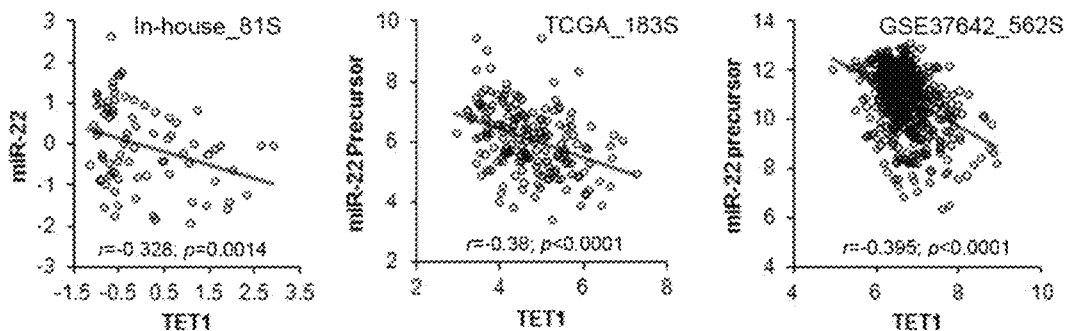
FIGS. 5A-5G establish a transcriptional correlation between miR-22 and TET1.
Figure 5B:
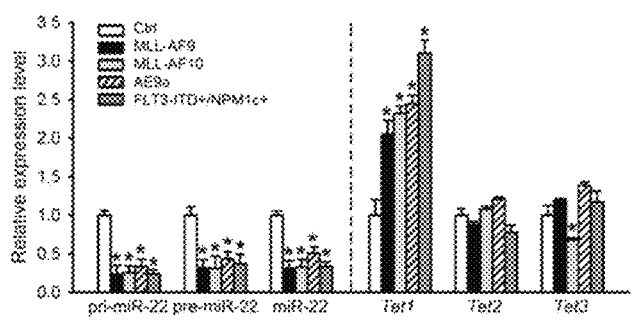
Figure 5C:
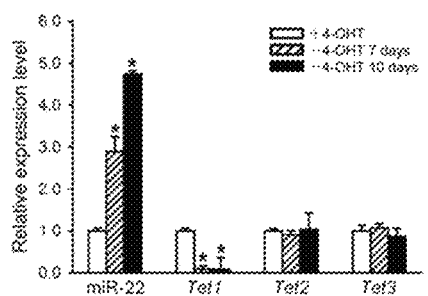

It was reported that TET2 is repressed by miR-22 as its direct target in breast cancer and MDS[15, 16]. Here we analyzed the expression patterns of TET1/2/3 and miR-22 in three independent AML patient datasets[21, 22, 44] ENREF 30 ENREF 53 (Table 3). To our surprise, we found that TET2 (and likely also TET3) exhibited a positive correlation, whereas only TET1 exhibited a negative correlation, with miR-22 in expression in AML (Table 3; FIG. 5A). The primary, precursor and mature miR-22 levels were all significantly down-regulated by MLL-AF9, MLL-AF10, AE9a, and FLT3-ITD/NPM1c+ in colony-forming cells, while Tet1 (but not Tet2 or Tet3) was up-regulated (FIG. 5B). Conversely, in MLL-ENL-ERtm cells[31], Tet1, but not Tet2 or Tet3, was down-regulated when miR-22 was up-regulated after withdrawal of 4-OHT (FIG. 5C). Thus, Tet1, instead of Tet2, exhibited an inverse correlation with miR-22 in expression in both human and mouse leukemic cells. Tet1 also exhibits an inverse correlation with miR-22 in expression during mouse normal myeloid differentiation (FIG. 11A). Furthermore, as miR-22 and TET1 were expressed at a significantly higher and lower level, respectively, in human normal CD33+ myeloid progenitor cells than in CD34+ HSPCs or MNCs (see FIG. 1A and Ref.[14]), the inverse expressional correlation between miR-22 and TET1 likely also existed in human normal hematopoietic cells.

Figure 5D:
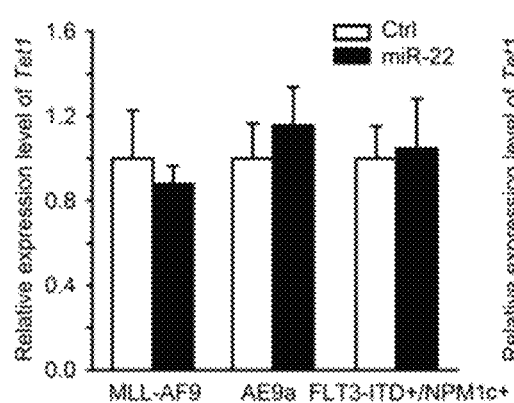
Figure 5E:
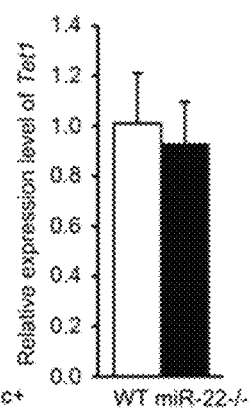
Figure 5F:
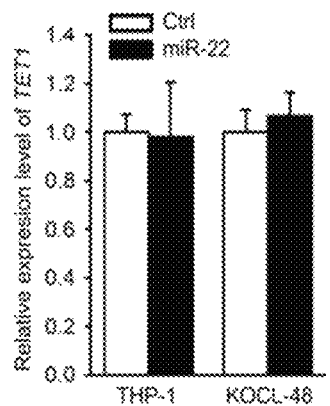
Figure 5G:
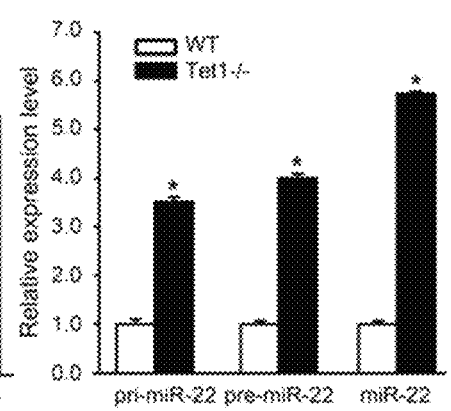

However, forced expression of miR-22 caused no noticeable changes in Tet1 expression in MLL-AF9, AE9a, or FLT3-ITD/NPM1c+ colony-forming cells (FIG. 5D). Similarly, neither miR-22 knockout nor overexpression resulted in any significant changes of Tet1/TET1 expression (FIGS. 5E, 5F). In contrast, Tet1 knockout remarkably increased the levels of pri-, pre- and mature miR-22 (FIG. 5G). Thus, the data suggest that miR-22 is a downstream target of and negatively regulated by Tet1, and that there is no negative feedback of miR-22 on Tet1 expression.

Figure 6A:
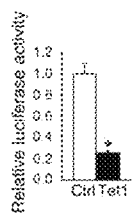
FIGS. 6A-6H evidence that TET1 mediates epigenetic repression of miR-22 transcription.
Figure 6B:
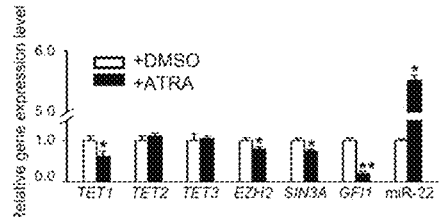
Figure 12A:
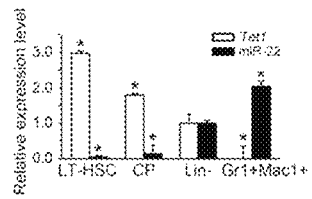
FIG. 12A-FIG. 12K evidence involvement of TET1 in miR-22 regulation.
Figure 12B:

Tet1 has been shown to cooperate with Polycomb repressive complex 2 (PRC2) components and cofactors, such as Ezh2 and Sin3a, to repress transcription of their co-target genes in mouse embryonic stem cells[8, 9]. Our luciferase reporter assay showed that forced expression of Tet1 significantly repressed the transcriptional activity controlled by the miR-22 promoter[45], suggesting that miR-22 is a direct repressed target of Tet1 (FIG. 6A). In an all-trans retinoic acid (ATRA)-induced THP-1/t(9;11) monocytic differentiation model[46], we showed that upon treatment with ATRA, TET1 (but not TET2 or TET3), EZH2 and SIN3A were significantly down-regulated, accompanied by the up-regulation of miR-22 (FIG. 6B). WDR81 is the gene that is located closely (within 500 bp) but oppositely to the miR-22 gene loci (see FIG. 6D). We also tested the potential influence of ATRA on the expression level of WDR81 in the same model. ATRA treatment showed no significant effects on WDR81 level (FIG. 12B), suggesting that TET1 specifically inhibits the transcription of miR-22, but not its neighboring gene with the opposite orientation.

While miR-22 expression level had a more than 5-fold increase upon ATRA treatment, the degrees of decrease in expression levels of TET1, EZH2 and SIN3A are relatively mild (though statistically significant) (FIG. 6B). To identify additional transcription factor(s) that is (are) more responsive to ATRA treatment and can facilitate TET1 binding to miR-22 promoter region, we searched for transcription factors that have evolutionarily conserved binding sites within the CpG island of miR-22 locus. Amongst a set of such transcription factors (including GFI1, STAT, PAX4, HMX1, and SRF), only GFI1 exhibited a significant inverse correlation with miR-22 in expression in all large-scale AML cohorts (Table 3). Interestingly, it was reported previously that ATRA treatment could significantly diminish the binding of GFI1 to the loci of many of its target genes, e.g., IL-6R, JAK3, E2F6, etc.[47] Thus, we chose GFI1 for further studies.

Figure 6C:
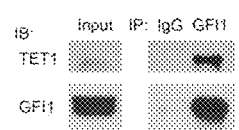
Figure 6D:
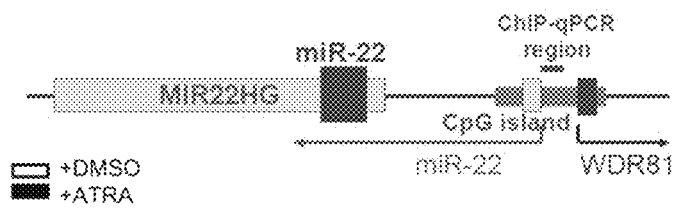
Figure 6E:
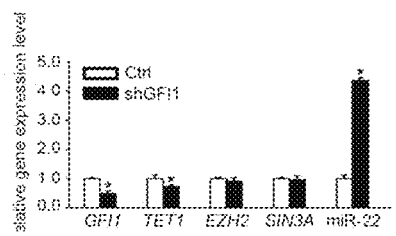
Figure 6F:
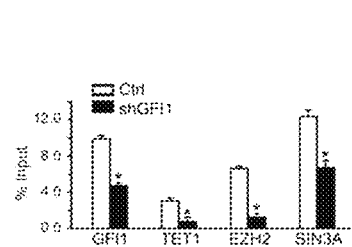
Figure 6G:
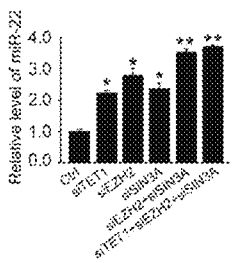
Figure 12C:
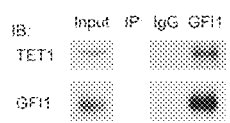
Figure 12D:
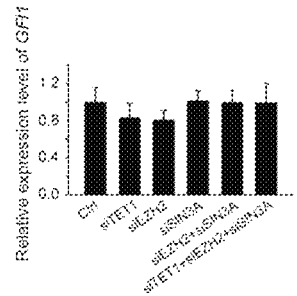
Figure 12E:
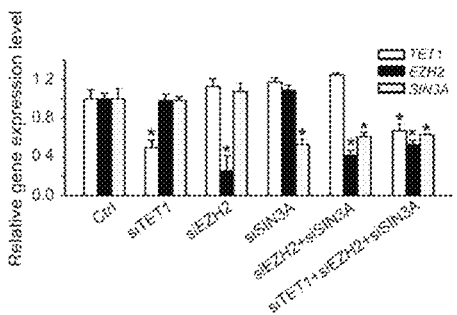
Figure 12F:
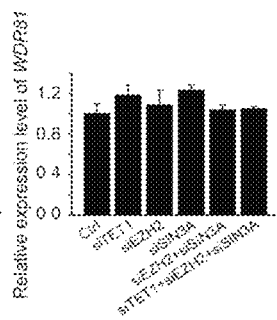
Figure 12G:

Notably, it was found that ATRA treatment substantially reduced the transcription level of GFI1 in AML cells and its decrease degree was greater than that of TET1, EZH2 or SIN3A (FIG. 6B). It was further shown that GFI1 is a binding partner of TET1 in both THP1 and HEK293T cells (FIG. 6C; FIG. 12C). ATRA treatment remarkably reduced the binding of GFI1, TET1, EZH2 and SIN3A, but not that of MLL protein, to the miR-22 promoter region (FIG. 6D). H3K27me3 modifications and RNA polymerase II (RNA pol II) occupancy were significantly decreased and increased, respectively, while H3K4Me3 modifications showed no significant change (FIG. 6D). Noticeably, the enrichment of GFI1 to this region was diminished by ATRA to a greater degree than that of TET1, EZH2 or SIN3A (FIG. 6D), suggesting that GFI1 might be the primary effector of ATRA treatment in regulating miR-22 expression. Consistently, knockdown of GFI1 resulted in a dramatic increase in miR-22 expression (>4 fold; FIG. 6E), associated with a significant decrease in the binding of TET1, EZH2, SIN3A, and GFI1 itself to the miR-22 promoter region (FIG. 6F). Knockdown of expression of TET1, EZH2 or SIN3A resulted in a 2-3 fold increase in miR-22 expression (FIG. 6G), with no effects on GFI1 expression (FIG. 12D); only their combinational knockdown could cause a similar level of increase in miR-22 expression (FIG. 6G; FIG. 12E) to that induced by GFI1 knockdown (FIG. 6E). As expected, the expression level of WDR81 was not changed upon knockdown of GFI1, TET1, EZH2 or SIN3A (FIGS. 12F and 12G). The data suggest that GFI1, TET1, EZH2 and SIN3A are all involved in transcriptional repression of miR-22 expression; and when treated with ATRA, GFI1 likely functions as the primary effector that facilitates the binding of TET1/EZH2/SIN3A complex to the miR-22 promoter region.

Figure 12H:
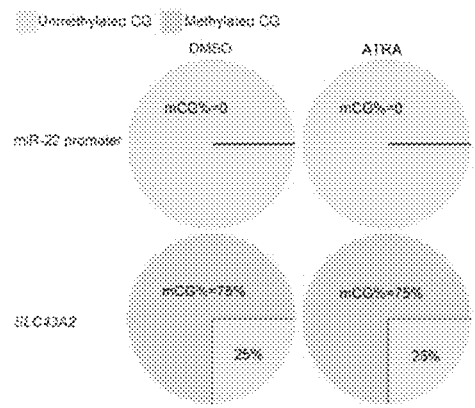
Figure 12I:
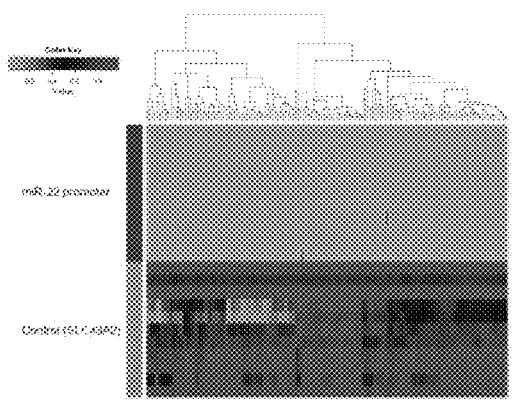
Figure 12J:
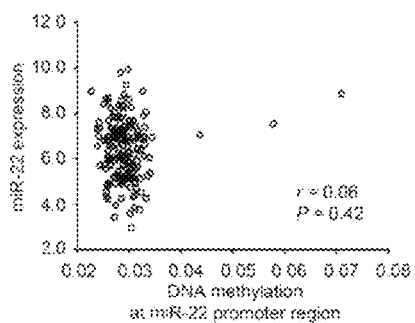

As TET1 is a methylcytosine dioxygenase[8, 9, 10], bisulfite sequencing analysis was conducted to investigate whether TET1 affects the methylation status of the miR-22 promoter. The analysis showed that the miR-22 promoter was hypomethylated in AML cells, no matter treated with or without ATRA (FIG. 12H). The hypomethylated status of the miR-22 promoter region in various AML was confirmed by analyzing the TCGA_194S dataset with DNA methylation information (FIG. 12I). The methylation status of the miR-22 promoter showed no significant correlation with miR-22 expression level in AML (FIG. 12J). These data suggest that the hypomethylation status of miR-22 promotor region does not lead to a high level expression of miR-22 in AML, and TET1-mediated repression of miR-22 transcription is unlikely related to its methylcytosine dioxygenase activity.

TABLE 3

Correlation between miR-22 and TET1/2/3 or GFI1 in expression in three AML patient cohorts*

| AML set | Gene | r | p |
|---|---|---|---|
| In-house_81S (n = 81) | TET1 | −0.328 | 0.0014 |
| | TET2 | 0.239 | 0.016 |
| | TET3 | 0.013 | 0.45 |
| | GFI1 | −0.429 | <0.0001 |
| TCGA_183S (n = 183) | TET1 | −0.380 | <0.0001 |
| | TET2 | 0.356 | <0.0001 |
| | TET3 | 0.327 | <0.0001 |
| | GFI1 | −0.249 | 0.0007 |
| GSE37642_562S (n = 562) | TET1 | −0.395 | <0.0001 |
| | TET2 | 0.140 | 0.0009 |
| | TET3 | 0.294 | <0.0001 |
| | GFI1 | −0.262 | 0.0005 |

*Pearson Correlation analysis of TET1/2/3 or GFI1 with mature miR-22 (for In-house_81S) or precursor miR-22 (for TCGA_183S and GSE37642_562S) in expression was performed.
r, correlation coefficient; p, p-value.

Example 7

The miR-22-associated Regulatory Circuit in AML

Figure 12K:
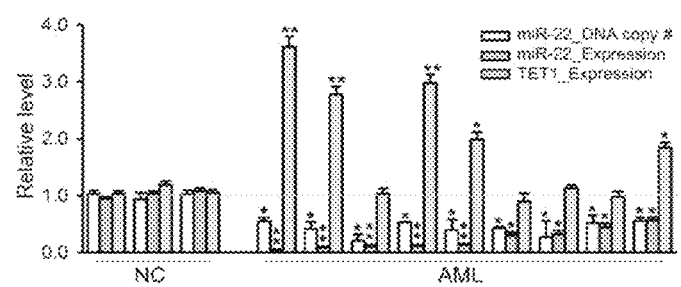

The foregoing data suggest that repression of miR-22 in AML is attributed to both DNA copy-number loss and especially TET1-mediated transcriptional suppression. Interestingly, amongst the 9 AML samples with DNA copy-number loss of miR-22 locus (FIGS. 11A, 11B), the AML samples with both copy-number loss and TET1 overexpression generally exhibited a more significant repression of miR-22 expression than those with copy-number loss alone (FIG. 12K). Thus, those two mechanisms are not mutually exclusive and can have synergistic effect on reducing miR-22 expression.

Figure 6H:
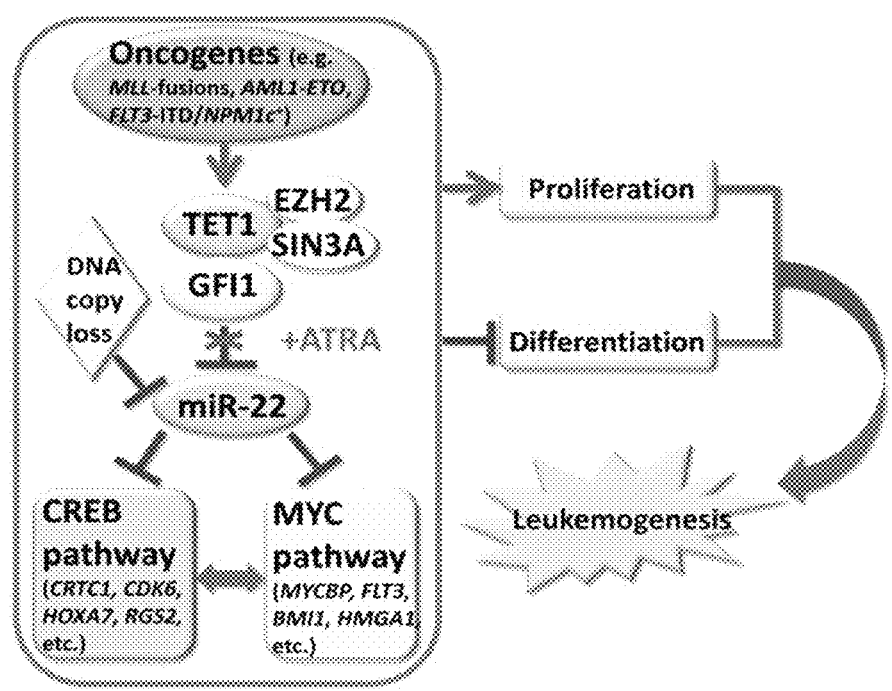

Collectively, these studies revealed a previously unappreciated genetic/epigenetic regulatory circuit in AML (FIG. 6H). In this circuit, oncogenic fusion genes or gene mutants (e.g., MLL-fusions, AE9a, and FLT3-ITD/NPM1c[+]) function as the "drivers". They promote the expression of TET1, which in turn, through recruiting polycomb cofactors such as EZH2 and SIN3A, represses the transcription of miR-22 by increasing H3K27me3 and decreasing RNA Pol II binding at the miR-22 promoter. When AML cells are treated with ATRA, ATRA substantially diminishes the enrichment of GFI1, a binding partner of TET1, at the miR-22 promoter, and thereby inhibits the recruitment of the TET1/EZH2/SIN3A complex to this region. In addition, miR-22 can also be compromised in its function by genetic mechanism(s) such as DNA copy-number loss in a portion (7%-18%) of the AML cases. The inactivation of miR-22 results in the de-repression of its critical oncogenic targets such as CRCT1, MYCBP and FLT3, and thereby the activation of both CREB and MYC signaling pathways, leading to cell transformation and leukemogenesis.

Example 8

Restoration of miR-22 Expression and Function to Treat AML

Figure 7D:
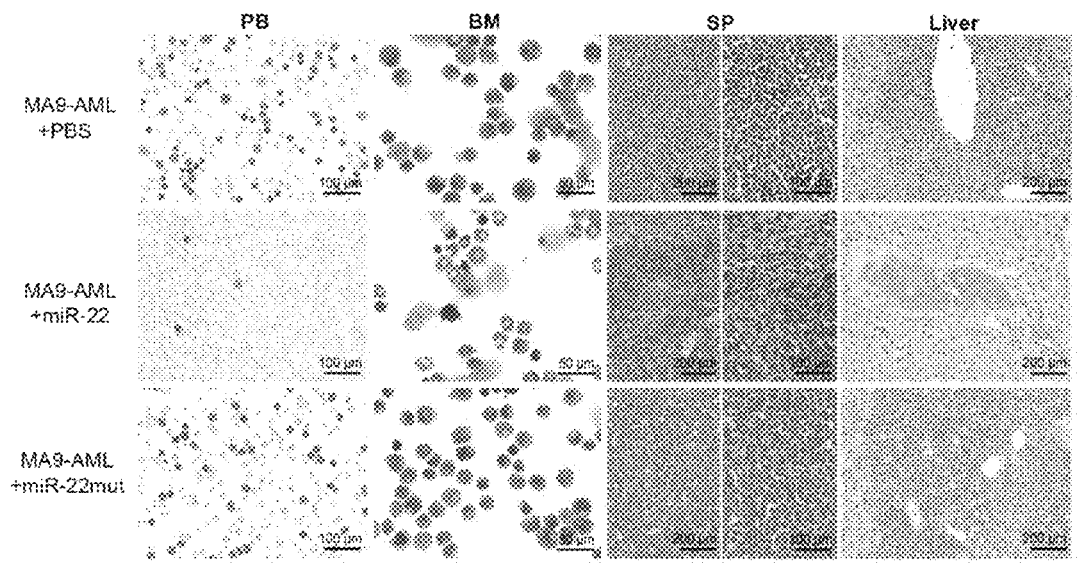
Figure 13A:
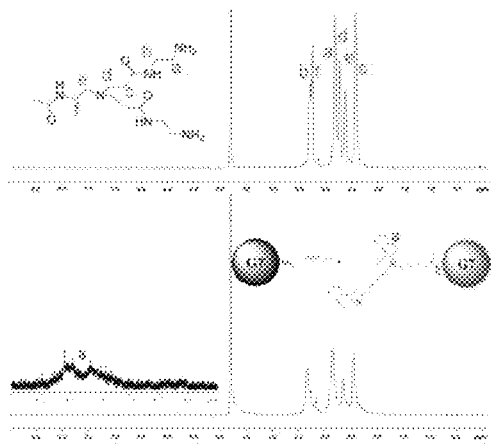
FIG. 13A-FIG. 13E illustrates the formation and effects of G7-Cy5.5-NH$_2$-miR-22 nanoparticles.
Figure 13B:
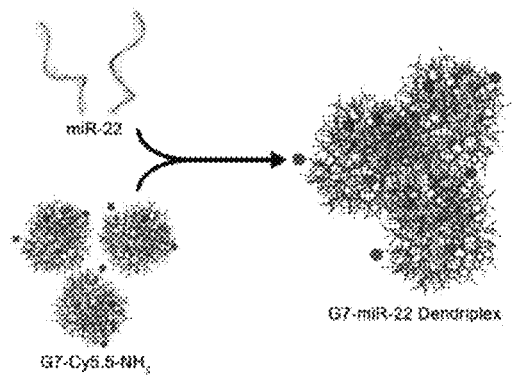
Figure 13C:
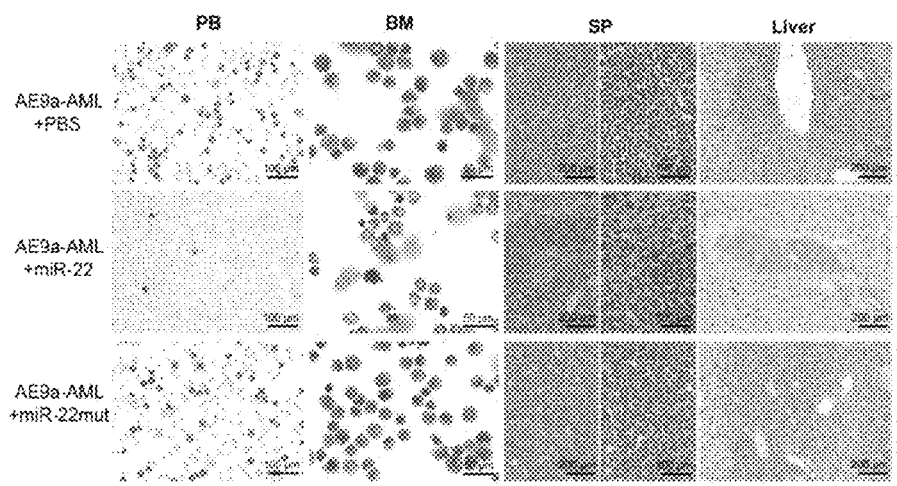
Figure 13D:
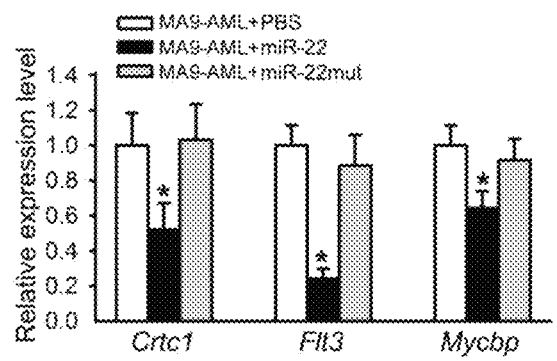

To investigate the therapeutic potential of restoration of miR-22 expression/function in treating AML, amine-terminated, generation 7 (G7) poly(amidoamine) (PAMAM) dendrimers were developed and employed as (FIGS. 6A and 6B) an effective non-viral gene delivery vector with minimal side effects[48]. Nanoparticles carrying miR-22 oligos significantly delayed AML progression in both MLL-AF9 and AE9a-induced secondary leukemic recipients (FIGS. 7A and 7B). Notably, at least 40% of the treated mice seemed to be completely cured by the miR-22 nanoparticles as the pathological morphologies in PB, BM, spleen and liver tissues all became normal (FIG. 7D; FIG. 13C). In contrast, the miR-22 mutant nanoparticles exhibited no significant therapeutic effect (FIGS. 7A, 7B and 7D; FIG. 13C). As expected, miR-22 oligos, but not miR-22 mutant oligos, significantly inhibited expression of its critical targets (i.e., Crct1, Flt3 and Mycbp) in BM cells of the treated mice (FIG. 13D). The miR-22-nanoparticles showed no noticeable effects on blood cell lineages (Table 4).

Figure 13E:
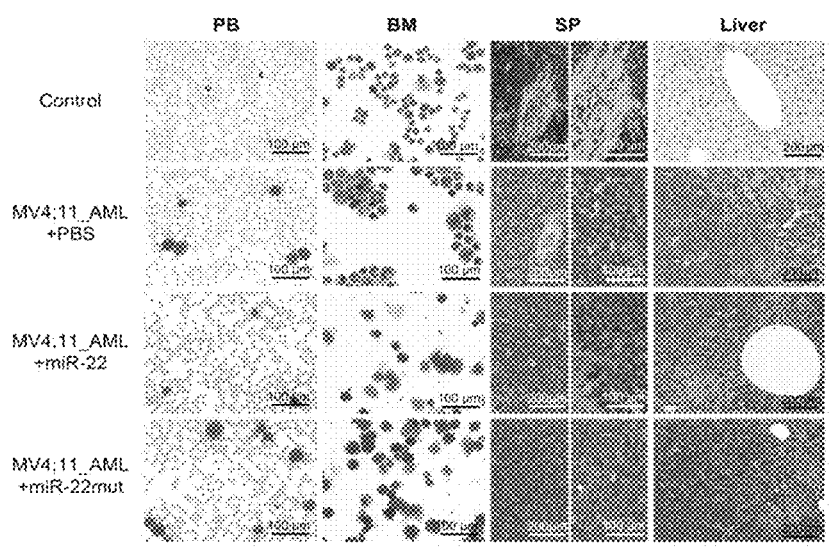
Figure 14:
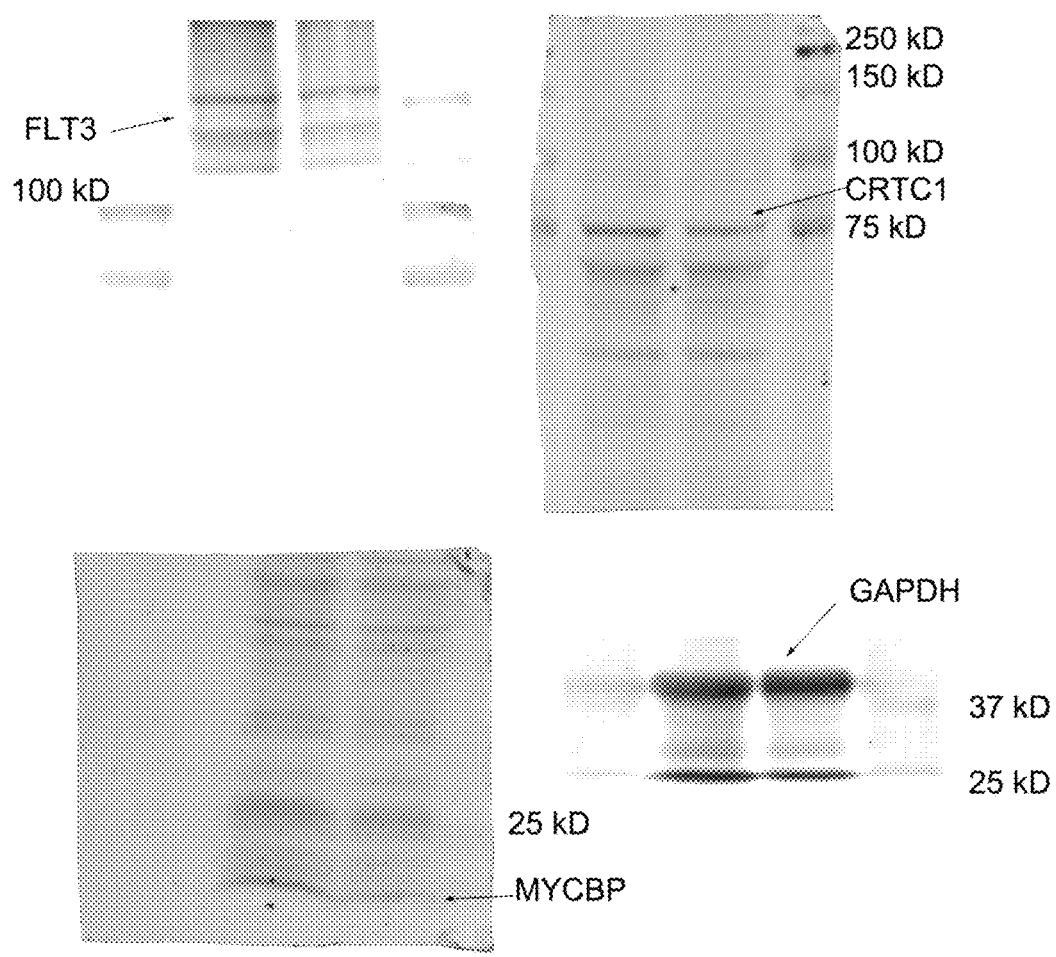
FIG. 14 sets forth original scans of Western blotting results shown as FIG. 10B.
Figure 15:
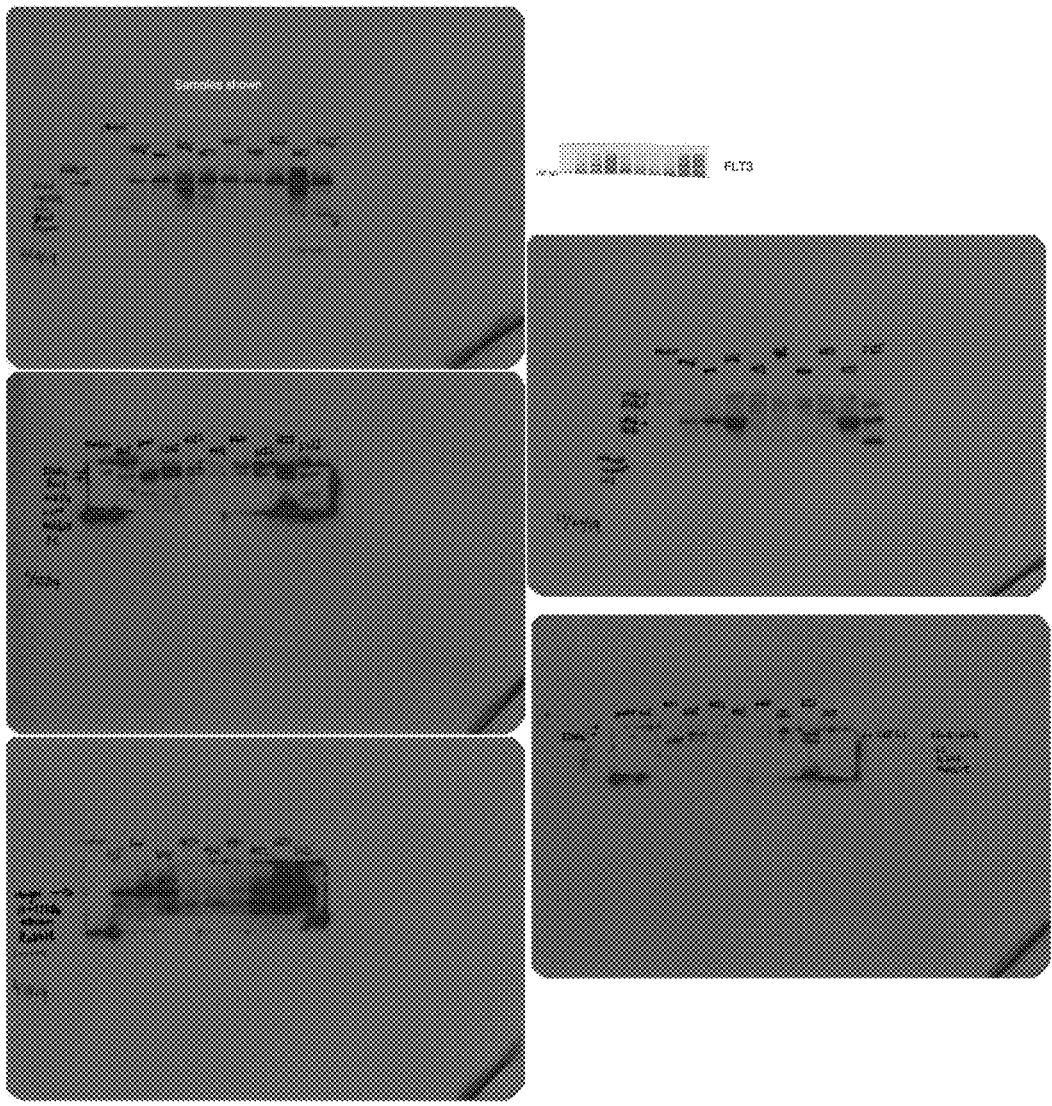
FIG. 15 sets forth original scans of Western blotting results shown as FIG. 10C.
Figure 16:
FIG. 16 sets forth original scans of Western blotting results shown as FIG. 13C.

The miR-22 nanoparticles were then tested in a xeno-transplantation model[49]. Similarly, the nanoparticles carrying miR-22 oligos, but not miR-22 mutant, significantly delayed AML progression induced by human MV4;11/t(4; 11) cells (FIG. 7C). The miR-22-nanoparticle administration also resulted in less aggressive leukemic pathological phenotypes in the recipient mice (FIG. 13E). Thus, these studies demonstrate the therapeutic potential of using miR-22-based nanoparticles to treat AML.

TABLE 4

Effects of G7-miR-22-nanoparticles on mouse blood cell differentiation.

| | 4 W | | 8 W | | 12 W | | 16 W | | 20 W | | Normal |
|---|---|---|---|---|---|---|---|---|---|---|---|
| | PBS | miR-22 | PBS | miR-22 | PBS | miR-22 | PBS | miR-22 | PBS | miR-22 | range |
| WBC (K/μl) | 12.26 | 11.92 | 12.06 | 8.92 | 4.14 | 4.18 | 8.71 | 9.18 | 5.74 | 6.7 | 1.8-10.7 |
| NE (K/μl) | 2.79 | 2.04 | 2.33 | 1.85 | 0.57 | 0.06 | 1.16 | 0.61 | 0.68 | 0.88 | 0.1-2.4 |
| LY (K/μl) | 8.3 | 9.48 | 8.87 | 6.59 | 3.38 | 3.97 | 6.95 | 7.97 | 4.67 | 5.24 | 0.9-9.3 |
| MO (K/μl) | 0.43 | 0.3 | 0.5 | 0.46 | 0.12 | 0.14 | 0.36 | 0.29 | 0.33 | 0.44 | 0.0-0.4 |
| EO (K/μl) | 0.57 | 0.08 | 0.25 | 0.02 | 0.05 | 0 | 0.19 | 0.23 | 0.05 | 0.1 | 0.0-0.2 |
| BA (K/μl) | 0.16 | 0.01 | 0.11 | 0.01 | 0.01 | 0 | 0.06 | 0.09 | 0.01 | 0.03 | 0.0-0.2 |
| RBC (M/μl) | 11.68 | 10.74 | 12.2 | 10.57 | 9.41 | 11.78 | 11.51 | 12.35 | 7.71 | 9.41 | 6.36-9.42 |
| PLT (K/μl) | 728 | 875 | 847 | 1215 | 1253 | 1246 | 1007 | 1354 | 1070 | 873 | 592-2972 |

Note:
Shown are data collected at the indicated time points (i.e. 4, 8, 12, 16 and 20 weeks) post single i.v. injection of 0.5 mg/kg of G7-miR-22-nanoparticles (miR-22) or PBS control (PBS).
WBC = white blood cells;
NE = neutrophils;
LY = lymphocytes;
MO = monocytes;
EO = eosinophils;
BA = basophils;
RBC = red blood cells;
PLT = platelets.

Example 9

The following example illustrates development of FLT3L-conjugated Generation 7 (G7) PAMAM (G7-FLT3L) dendrimers for selective delivery of miR-22 to AML cells based on methodology disclosed by the present inventors set forth in PCT/US2017/037424, the entire disclosure of which is incorporated herein by this citation.

In order to selectively deliver miR-22 oligos to FLT3-expressing AML cells, Poly(amidoamine) (PAMAM) dendrimers (Hong S, et al. *Bioconjugate Chemistry.* 2006; 17:728-34, Hong S, et al. *Bioconjugate Chemistry.* 2009; 20:1503-13, and Sunoqrot S, et al. *J Control Release.* 2014; 191:115-22, incorporated herein by reference) are selected as the basis of the nanoparticle carriers, and conjugated with the near-infrared dye Cyanine 5.5 (Cy5.5) for monitoring the dynamic distributions of the nanoparticles, and FLT3 ligand (FLT3L) proteins for specific targeting FLT3 on the cell surface. H2B, a nuclear histone protein with similar molecular weight as FLT3L, was conjugated as a negative control. G7-FLT3L dendrimers will efficiently and selectively target AML cells with FLT3 overexpression. After 24 hours' treatment of the nanoparticles, the uptake ratios of the G7-FLT3L dendrimers are significantly higher than the G7-H2B control nanoparticles in MONOMAC-6 cells, an AML cell line carrying the t(9;11)/MLL-AF9 (i.e., the most common form of MLL-rearranged AML (Krivtsov A V, et al. *Nat Rev Cancer.* 2007; 7:823-33 and Slany R K. *Haematologica.* 2009; 94:984-93, both incorporated by reference)).

The nanoparticles are taken up in a dose dependent manner. In addition, the cellular uptake of G7-FLT3L nanoparticles by FLT3-overexpressing AML cells is rapid. The one-hour uptake ratio of G7-FLT3L dendrimers is 23.6%, significantly higher than that (5.9%) of G7-H2B dendrimers. In contrast, the uptake ratios between G7-FLT3L and G7-H2B dendrimers showed no significant difference in U937 cells (a cell line with very low levels of FLT).

Whether the high level of FLT3 expression of target cells is required for the high uptake ratio of G7-FLT3L nanoparticles is determined. Suppression of endogenous FLT3 expression in MONOMAC-6 cells by overexpressing miR-22 results in a significant decrease of the uptake ratio of G7-FLT3L nanoparticles, but not that of G7-H2B nanoparticles. Neither G7-FLT3L nor G7-H2B dendrimers show significant effects on the viability and apoptosis of MONO-MAC-6 cells as compared with PBS, indicating low, if any, cytotoxicity of both dendrimer constructs.

Collectively, the above results indicate that G7-FLT3L nanoparticles can rapidly, efficiently, and selectively target FLT3-overexpressing AML cells, with minimal non-specific cellular toxicity, and thereby deliver molecules complexed therewith, such as miR-22, directly to AML cells.

The entire disclosures of the following references are incorporated herein by citation. Inclusion of a reference in this list of references is for background, methodology, and clarity purposes and should not be construed one was or the other as an indication or admission of relevance to patentability.

1. Zeisig B B, Kulasekararaj A G, Mufti G J, So C W. SnapShot: Acute myeloid leukemia. *Cancer Cell* 22, 698-698 e691 (2012).
2. Estey E, Dohner H. Acute myeloid leukaemia. *Lancet* 368, 1894-1907 (2006).
3. Grimwade D, Mrozek K. Diagnostic and prognostic value of cytogenetics in acute myeloid leukemia. *Hematology/oncology clinics of North America* 25, 1135-1161, vii (2011).
4. Chen J, Odenike O, Rowley J D. Leukaemogenesis: more than mutant genes. *Nat Rev Cancer* 10, 23-36 (2010).
5. Graubert T, Walter M J. Genetics of myelodysplastic syndromes: new insights. *Hematology Am Soc Hematol Educ Program* 2011, 543-549 (2011).
6. Figueroa M E, et al. MDS and secondary AML display unique patterns and abundance of aberrant DNA methylation. *Blood* 114, 3448-3458 (2009).

7. Griffiths E A, Gore S D. Epigenetic therapies in MDS and AML. *Adv Exp Med Biol* 754, 253-283 (2013).
8. Wu H, et al. Dual functions of Tet1 in transcriptional regulation in mouse embryonic stem cells. *Nature* 473, 389-393 (2011).
9. Williams K, et al. TET1 and hydroxymethylcytosine in transcription and DNA methylation fidelity. *Nature* 473, 343-348 (2011).
10. Hu X, et al. Tet and TDG mediate DNA demethylation essential for mesenchymal-to-epithelial transition in somatic cell reprogramming *Cell Stem Cell* 14, 512-522 (2014).
11. Delhommeau F, et al. Mutation in TET2 in myeloid cancers. *N Engl J Med* 360, 2289-2301 (2009).
12. Ko M, et al. Impaired hydroxylation of 5-methylcytosine in myeloid cancers with mutant TET2. *Nature* 468, 839-843 (2010).
13. Moran-Crusio K, et al. Tet2 loss leads to increased hematopoietic stem cell self-renewal and myeloid transformation. *Cancer Cell* 20, 11-24 (2011).
14. Huang H, et al. TET1 plays an essential oncogenic role in MLL-rearranged leukemia. *Proc Natl Acad Sci USA* 110, 11994-11999 (2013).
15. Song S J, et al. MicroRNA-antagonism regulates breast cancer stemness and metastasis via TET-family-dependent chromatin remodeling. *Cell* 154, 311-324 (2013).
16. Song S J, et al. The oncogenic microRNA miR-22 targets the TET2 tumor suppressor to promote hematopoietic stem cell self-renewal and transformation. *Cell Stem Cell* 13, 87-101 (2013).
17. Jiang X, et al. Blockade of miR-150 Maturation by MLL-Fusion/MYC/LIN-28 Is Required for MLL-Associated Leukemia. *Cancer Cell* 22, 524-535 (2012).
18. Lewis B P, Burge C B, Bartel D P. Conserved seed pairing, often flanked by adenosines, indicates that thousands of human genes are microRNA targets. *Cell* 120, 15-20 (2005).
19. Yan M, et al. A previously unidentified alternatively spliced isoform of t(8;21) transcript promotes leukemogenesis. *Nat Med* 12, 945-949 (2006).
20. Gurha P, et al. Targeted deletion of microRNA-22 promotes stress-induced cardiac dilation and contractile dysfunction. *Circulation* 125, 2751-2761 (2012).
21. He C, Li Z, Chen P, Huang H, Hurst L D, Chen J. Young intragenic miRNAs are less coexpressed with host genes than old ones: implications of miRNA-host gene coevolution. *Nucleic Acids Res* 40, 4002-4012 (2012).
22. Ley T J, et al. Genomic and epigenomic landscapes of adult de novo acute myeloid leukemia. *N Engl J Med* 368, 2059-2074 (2013).
23. Li Z, et al. miR-196b directly targets both HOXA9/MEIS1 oncogenes and FAS tumour suppressor in MLL-rearranged leukaemia. *Nat Commun* 2, 688 (2012).
24. Wang Z, et al. GSK-3 promotes conditional association of CREB and its coactivators with MEIS1 to facilitate HOX-mediated transcription and oncogenesis. *Cancer Cell* 17, 597-608 (2010).
25. Cheng J C, et al. CREB is a critical regulator of normal hematopoiesis and leukemogenesis. *Blood* 111, 1182-1192 (2008).
26. Sandoval S, Pigazzi M, Sakamoto K M. CREB: A Key Regulator of Normal and Neoplastic Hematopoiesis. *Adv Hematol* 2009, 634292 (2009).
27. Haferlach C, et al. ETV6 rearrangements are recurrent in myeloid malignancies and are frequently associated with other genetic events. *Genes Chromosomes Cancer* 51, 328-337 (2012).
28. Armstrong S A, et al. Inhibition of FLT3 in MLL. Validation of a therapeutic target identified by gene expression based classification. *Cancer Cell* 3, 173-183 (2003).
29. Takahashi S. Downstream molecular pathways of FLT3 in the pathogenesis of acute myeloid leukemia: biology and therapeutic implications. *J Hematol Oncol* 4, 13 (2011).
30. Xiong J, Du Q, Liang Z. Tumor-suppressive microRNA-22 inhibits the transcription of E-box-containing c-Myc target genes by silencing c-Myc binding protein. *Oncogene* 29, 4980-4988 (2010).
31. Zeisig B B, et al. Hoxa9 and Meis1 are key targets for MLL-ENL-mediated cellular immortalization. *Mol Cell Biol* 24, 617-628 (2004).
32. Pigazzi M, et al. MicroRNA-34b promoter hypermethylation induces CREB overexpression and contributes to myeloid transformation. *Haematologica* 98, 602-610 (2013).
33. Placke T, et al. Requirement for CDK6 in MLL-rearranged acute myeloid leukemia. *Blood* 124, 13-23. (2014).
34. Ayton P M, Cleary M L. Transformation of myeloid progenitors by MLL oncoproteins is dependent on Hoxa7 and Hoxa9. *Genes Dev* 17, 2298-2307 (2003).
35. Schwable J, et al. RGS2 is an important target gene of Flt3-ITD mutations in AML and functions in myeloid differentiation and leukemic transformation. *Blood* 105, 2107-2114 (2005).
36. Smith L L, et al. Functional crosstalk between Bmi1 and MLL/Hoxa9 axis in establishment of normal hematopoietic and leukemic stem cells. *Cell Stem Cell* 8, 649-662 (2011).
37. Wu X, Qin L, Fako V, Zhang J T. Molecular mechanisms of fatty acid synthase (FASN)-mediated resistance to anti-cancer treatments. *Adv Biol Regul* 54, 214-221 (2014).
38. Xu Y, et al. The HMG-I oncogene causes highly penetrant, aggressive lymphoid malignancy in transgenic mice and is overexpressed in human leukemia. *Cancer Res* 64, 3371-3375 (2004).
39. Jacoby M A, Walter M J Detection of copy number alterations in acute myeloid leukemia and myelodysplastic syndromes. *Expert Rev Mol Diagn* 12, 253-264 (2012).
40. Ninomiya S, et al. Integrated analysis of gene copy number, copy neutral LOH, and microRNA profiles in adult acute lymphoblastic leukemia. *Cytogenet Genome Res* 136, 246-255 (2012).
41. Konishi H, et al. Detailed characterization of a homozygously deleted region corresponding to a candidate tumor suppressor locus at distal 17p13.3 in human lung cancer. *Oncogene* 22, 1892-1905 (2003).
42. Sankar M, et al. Identification of a commonly deleted region at 17p13.3 in leukemia and lymphoma associated with 17p abnormality. *Leukemia* 12, 510-516 (1998).
43. Chattopadhyay P, Rathore A, Mathur M, Sarkar C, Mahapatra A K, Sinha S. Loss of heterozygosity of a locus on 17p13.3, independent of p53, is associated with higher grades of astrocytic tumours. *Oncogene* 15, 871-874 (1997).
44. Li Z, et al. Identification of a 24-gene prognostic signature that improves the European LeukemiaNet risk classification of acute myeloid leukemia: an international collaborative study. *J Clin Oncol* 31, 1172-1181 (2013).
45. Bar N, Dikstein R. miR-22 forms a regulatory loop in PTEN/AKT pathway and modulates signaling kinetics. *PLoS One* 5, e10859 (2010).

46. Drach J, Lopez-Berestein G, McQueen T, Andreeff M, Mehta K. Induction of differentiation in myeloid leukemia cell lines and acute promyelocytic leukemia cells by liposomal all-trans-retinoic acid. *Cancer Res* 53, 2100-2104 (1993).

47. Duan Z, Horwitz M. Targets of the transcriptional repressor oncoprotein Gfi-1. *Proc Natl Acad Sci USA* 100, 5932-5937 (2003).

48. Pack D W, Hoffman A S, Pun S, Stayton P S. Design and development of polymers for gene delivery. *Nat Rev Drug Discov* 4, 581-593 (2005).

49. Wunderlich M, et al. AML xenograft efficiency is significantly improved in NOD/SCID-IL2RG mice constitutively expressing human SCF, GM-CSF and IL-3. *Leukemia* 24, 1785-1788 (2010).

50. Cartron P F, Nadaradjane A, Lepape F, Lalier L, Gardie B, Vallette F M. Identification of TET1 Partners That Control Its DNA-Demethylating Function. *Genes Cancer* 4, 235-241 (2013).

51. Saleque S, Kim J, Rooke H M, Orkin S H. Epigenetic regulation of hematopoietic differentiation by Gfi-1 and Gfi-1b is mediated by the cofactors CoREST and LSD1. *Mol Cell* 27, 562-572 (2007).

52. Thambyrajah R, et al. GFI1 proteins orchestrate the emergence of haematopoietic stem cells through recruitment of LSD1. *Nat Cell Biol* 18, 21-32 (2016).

53. Abdel-Wahab O, et al. Genetic characterization of TET1, TET2, and TET3 alterations in myeloid malignancies. *Blood* 114, 144-147 (2009).

54. Zuber J, et al. RNAi screen identifies Brd4 as a therapeutic target in acute myeloid leukaemia. *Nature* 478, 524-528 (2011).

55. Huang M J, Cheng Y C, Liu C R, Lin S, Liu H E. A small-molecule c-Myc inhibitor, 10058-F4, induces cell-cycle arrest, apoptosis, and myeloid differentiation of human acute myeloid leukemia. *Exp Hematol* 34, 1480-1489 (2006).

56. Ling H, Fabbri M, Calin G A. MicroRNAs and other non-coding RNAs as targets for anticancer drug development. *Nat Rev Drug Discov* 12, 847-865 (2013).

57. Li Z, et al. Distinct microRNA expression profiles in acute myeloid leukemia with common translocations. *Proc Natl Acad Sci USA* 105, 15535-15540 (2008).

58. Irizarry R A, Bolstad B M, Collin F, Cope L M, Hobbs B, Speed T P. Summaries of Affymetrix GeneChip probe level data. *Nucleic Acids Res* 31, e15 (2003).

59. Poliseno L, et al. Identification of the miR-106b-25 microRNA cluster as a proto-oncogenic PTEN-targeting intron that cooperates with its host gene MCM7 in transformation. *Sci Signal* 3, ra29 (2010).

60. Krivtsov A V, et al. Transformation from committed progenitor to leukaemia stem cell initiated by MLL-AF9. *Nature* 442, 818-822 (2006).

61. Somervaille T C, et al. Hierarchical maintenance of MLL myeloid leukemia stem cells employs a transcriptional program shared with embryonic rather than adult stem cells. *Cell Stem Cell* 4, 129-140 (2009).

62. Sekeres M J, et al. Increasing CRTC1 function in the dentate gyrus during memory formation or reactivation increases memory strength without compromising memory quality. *J Neurosci* 32, 17857-17868 (2012).

63. Jiang X, Yang P, Ma L. Kinase activity-independent regulation of cyclin pathway by GRK2 is essential for zebrafish early development. *Proc Natl Acad Sci USA* 106, 10183-10188 (2009).

64. Modi D A, Sunoqrot S, Bugno J, Lantvit D D, Hong S, Burdette J E. Targeting of follicle stimulating hormone peptide-conjugated dendrimers to ovarian cancer cells. *Nanoscale* 6, 2812-2820 (2014).

65. Mermel C H, Schumacher S E, Hill B, Meyerson M L, Beroukhim R, Getz G. GISTIC2.0 facilitates sensitive and confident localization of the targets of focal somatic copy-number alteration in human cancers. *Genome Biol* 12, R41 (2011).

66. Parkin B, et al. NF1 inactivation in adult acute myelogenous leukemia. *Clin Cancer Res* 16, 4135-4147 (2010).

67. Parkin B, et al. Acquired genomic copy number aberrations and survival in adult acute myelogenous leukemia. *Blood* 116, 4958-4967 (2010).

68. Wang K, et al. PennCNV: an integrated hidden Markov model designed for high-resolution copy number variation detection in whole-genome SNP genotyping data. *Genome Res* 17, 1665-1674 (2007).

69. Van Loo P, et al. Allele-specific copy number analysis of tumors. *Proc Natl Acad Sci USA* 107, 16910-16915 (2010).

70. Saeed A I, et al. TM4 microarray software suite. *Methods Enzymol* 411, 134-193 (2006).

---

The invention claimed is:

1. A nanoparticle delivery system designed for sustained delivery of microRNA-22(miR-22) to acute myeloid leukemia (AML) cells, the nanoparticle delivery system comprising poly(amidoamine) (PAMAM) dendrimers complexed with miR-22, wherein at least one dendrimer is surface-functionalized with a ligand specific for FLT3 receptor.

2. The delivery system according to claim 1, wherein the PAMAM dendrimers comprise between generation-2 and generation-8 dendrimers.

3. The delivery system according to claim 1, wherein the PAMAM dendrimers comprise generation 7 (G7) dendrimers.

4. The delivery system according to claim 1, wherein the ligand specific for FLT3 receptor comprises a natural or synthetic FLT3L peptide.

5. The delivery system according to claim 1, wherein the ligand specific for FLT3 receptor comprises a synthetic FLT3L peptide having at least 90% sequence homology to SEQ ID NO: 3.

6. The delivery system according to claim 5 wherein the synthetic FLT3L peptide is Flt3L peptide comprising SEQ ID NO: 3.

7. The delivery system according to claim 1, wherein the miR-22 is modified for stability.

8. The delivery system according to claim 7, wherein the miR-22 stability modification comprises 2'-O methylation.

9. The nanoparticle delivery system according to claim 1 comprising G7-Flt3L-(2'OMe)miR-22.

10. A pharmaceutical composition formulated as an injectable composition comprising a nanoparticle delivery system according to claim 1.

11. A method of treating a patient suffering from de novo acute myeloid leukemia (AML), the method comprising: administering to the patient a nanoparticle complex comprising poly(amidoamine) (PAMAM) dendrimers complexed with miR-22, wherein at least one dendrimer is surface-functionalized with a ligand specific for FLT3receptor.

12. The method according to claim 11, wherein the nanoparticle complex comprises a G2, G3, G4, G6 or G8-polyamidoamine (PAMAM) dendrimer.

13. The method according to claim 12, wherein the ligand specific for FLT3 receptor comprises a natural and/or synthetic FLT3L peptide.

14. The method according to claim 13, wherein the ligand specific for FLT3 receptor comprises a synthetic FLT3L peptide having at least 90% sequence homology to SEQ ID NO: 3.

15. The method according to claim 14, wherein the ligand specific for FLT3 receptor comprises Flt3L peptide consisting essentially of SEQ ID NO: 3.

16. The method according to claim 11, wherein the miR-22 comprises at least one stability modification.

17. The method according to claim 16, wherein the stability modification of miR-22comprises 2'-O methylation.

18. The method according to claim 11, wherein the nanoparticle complex is G7-Flt3L-(2'OMe)miR-22.

19. The method according to claim 11, wherein administering comprises systemic administration.

20. The method according to claim 19, wherein systemic administration comprises intravenous administration.

21. The method according to claim 11, further comprising administering at least one agent that directly or indirectly induces miR-22 expression.

22. The method according to claim 21, wherein the at least one agent is selected from all-trans-retinoic acid (ATRA) and NSC-370284.

23. The method according to claim 22, wherein the nanoparticle complex comprising miR-22 is administered before, after, or simultaneously with the at least one agent.

24. A method of treating a patient suffering from acute myeloid leukemia, the method comprising administering G7-Flt3L-(2'OMe)miR-22 to the patient.

* * * * *

SEQUENCE LISTING

```
<160> NUMBER OF SEQ ID NOS: 31

<210> SEQ ID NO 1
<211> LENGTH: 48
<212> TYPE: DNA
<213> ORGANISM: Mus musculus
<220> FEATURE:
<221> NAME/KEY: misc_feature
<223> OTHER INFORMATION: sno202 control sequence

<400> SEQUENCE: 1
gctgtactga cttgatgaaa gtacttttga acccttttcc atctgatg            48

<210> SEQ ID NO 2
<211> LENGTH: 22
<212> TYPE: RNA
<213> ORGANISM: Homo sapiens
<220> FEATURE:
<221> NAME/KEY: misc_feature
```

<223> OTHER INFORMATION: miR-22 sequence

<400> SEQUENCE: 2
aagcugccag uugaagaacu gu                                           22

<210> SEQ ID NO 3
<211> LENGTH: 74
<212> TYPE: PRT
<213> ORGANISM: Mus musculus
<220> FEATURE:
<221> NAME/KEY: MISC_FEATURE
<223> OTHER INFORMATION: Flt3L peptide

<400> SEQUENCE: 3

Ser Ser Asn Phe Lys Val Lys Phe Arg Glu Leu Thr Asp His Leu Leu
1               5                   10                  15

Lys Asp Tyr Pro Val Thr Val Ala Val Asn Leu Gln Asp Glu Lys His
            20                  25                  30

Cys Lys Ala Leu Trp Ser Leu Phe Leu Ala Gln Arg Trp Ile Glu Gln
        35                  40                  45

Leu Lys Thr Val Ala Gly Ser Lys Met Gln Thr Leu Leu Glu Asp Val
    50                  55                  60

Asn Thr Glu Ile His Phe Val Thr Ser Cys
65                  70

<210> SEQ ID NO 4
<211> LENGTH: 42
<212> TYPE: DNA
<213> ORGANISM: Homo sapiens
<220> FEATURE:
<221> NAME/KEY: misc_feature
<223> OTHER INFORMATION: RNU6B control sequence

<400> SEQUENCE: 4
cgcaaggatg acacgcaaat tcgtgaagcg ttccatattt tt                      42

<210> SEQ ID NO 5
<211> LENGTH: 24
<212> TYPE: DNA
<213> ORGANISM: Homo sapiens
<220> FEATURE:
<221> NAME/KEY: misc_feature
<223> OTHER INFORMATION: MSCV-PIG-miR-22 forward primer

<400> SEQUENCE: 5
gccctcgagt ctagactcca gttc                                         24

<210> SEQ ID NO 6
<211> LENGTH: 25
<212> TYPE: DNA
<213> ORGANISM: Homo sapiens
<220> FEATURE:
<221> NAME/KEY: misc_feature
<223> OTHER INFORMATION: MSCV-PIG-miR-22 reverse primer

<400> SEQUENCE: 6
ggggaattcc tactcctcaa tccag                                        25

<210> SEQ ID NO 7
<211> LENGTH: 26
<212> TYPE: DNA
<213> ORGANISM: Homo sapiens
<220> FEATURE:
<221> NAME/KEY: misc_feature
<223> OTHER INFORMATION: MSCV-PIG-MYCBP plasmid forward primer

```
<400> SEQUENCE: 7
aaactcgaga tggcccatta caaagc                                              26

<210> SEQ ID NO 8
<211> LENGTH: 22
<212> TYPE: DNA
<213> ORGANISM: Homo sapiens
<220> FEATURE:
<221> NAME/KEY: misc_feature
<223> OTHER INFORMATION: MSCV-PIG-MYCBP plasmid reverse primer

<400> SEQUENCE: 8
ccggaattcc tattcagcac gc                                                  22

<210> SEQ ID NO 9
<211> LENGTH: 24
<212> TYPE: DNA
<213> ORGANISM: Homo sapiens
<220> FEATURE:
<221> NAME/KEY: misc_feature
<223> OTHER INFORMATION: CRTC1 UTR forward primer

<400> SEQUENCE: 9
gccattacta gtcccacctg agtg                                                24

<210> SEQ ID NO 10
<211> LENGTH: 24
<212> TYPE: DNA
<213> ORGANISM: Homo sapiens
<220> FEATURE:
<221> NAME/KEY: misc_feature
<223> OTHER INFORMATION: CRTC1 UTR reverse primer

<400> SEQUENCE: 10
gccattaagc ttgaggacag aagc                                                24

<210> SEQ ID NO 11
<211> LENGTH: 33
<212> TYPE: DNA
<213> ORGANISM: Homo sapiens
<220> FEATURE:
<221> NAME/KEY: misc_feature
<223> OTHER INFORMATION: FLT3 UTR forward primer

<400> SEQUENCE: 11
gccgccacta gtaggaacaa tttagtttta agg                                      33

<210> SEQ ID NO 12
<211> LENGTH: 30
<212> TYPE: DNA
<213> ORGANISM: Homo sapiens
<220> FEATURE:
<221> NAME/KEY: misc_feature
<223> OTHER INFORMATION: FLT3 UTR reverse primer

<400> SEQUENCE: 12
cgcaagcttg tggggacaag agtaacttta                                          30

<210> SEQ ID NO 13
<211> LENGTH: 23
<212> TYPE: DNA
<213> ORGANISM: Homo sapiens
<220> FEATURE:
<221> NAME/KEY: misc_feature
<223> OTHER INFORMATION: miR-22 promoter region forward primer
```

<400> SEQUENCE: 13
aataatgagc tcaaggtcgg acg                                          23

<210> SEQ ID NO 14
<211> LENGTH: 25
<212> TYPE: DNA
<213> ORGANISM: Homo sapiens
<220> FEATURE:
<221> NAME/KEY: misc_feature
<223> OTHER INFORMATION: miR-22 promoter region reverse primer

<400> SEQUENCE: 14
aataatgata tcctttagct gggtc                                        25

<210> SEQ ID NO 15
<211> LENGTH: 19
<212> TYPE: DNA
<213> ORGANISM: Homo sapiens
<220> FEATURE:
<221> NAME/KEY: misc_feature
<223> OTHER INFORMATION: human miR-22 forward primer

<400> SEQUENCE: 15
gttgttggag tcgtgagtg                                               19

<210> SEQ ID NO 16
<211> LENGTH: 19
<212> TYPE: DNA
<213> ORGANISM: Homo sapiens
<220> FEATURE:
<221> NAME/KEY: misc_feature
<223> OTHER INFORMATION: human miR-22 reverse primer

<400> SEQUENCE: 16
cgctccacct ttccttaaa                                               19

<210> SEQ ID NO 17
<211> LENGTH: 17
<212> TYPE: DNA
<213> ORGANISM: Mus musculus
<220> FEATURE:
<221> NAME/KEY: misc_feature
<223> OTHER INFORMATION: mouse miR-22 forward primer

<400> SEQUENCE: 17
tgaatgggcg ggagtaa                                                 17

<210> SEQ ID NO 18
<211> LENGTH: 16
<212> TYPE: DNA
<213> ORGANISM: Mus musculus
<220> FEATURE:
<221> NAME/KEY: misc_feature
<223> OTHER INFORMATION: mouse miR-22 reverse primer

<400> SEQUENCE: 18
ccacgagctg cgaatg                                                  16

<210> SEQ ID NO 19
<211> LENGTH: 24
<212> TYPE: DNA
<213> ORGANISM: Homo sapiens
<220> FEATURE:
<221> NAME/KEY: misc_feature
<223> OTHER INFORMATION: miR-22 promoter forward primer

<400> SEQUENCE: 19
tttgtttatt tttgtttttt ggtt                                              24

<210> SEQ ID NO 20
<211> LENGTH: 21
<212> TYPE: DNA
<213> ORGANISM: Homo sapiens
<220> FEATURE:
<221> NAME/KEY: misc_feature
<223> OTHER INFORMATION: miR-22 promoter reverse primer

<400> SEQUENCE: 20
acaacccctc cttattaaaa t                                                 21

<210> SEQ ID NO 21
<211> LENGTH: 24
<212> TYPE: DNA
<213> ORGANISM: Homo sapiens
<220> FEATURE:
<221> NAME/KEY: misc_feature
<223> OTHER INFORMATION: SLC43A2 forward primer

<400> SEQUENCE: 21
tgttttgttt ttatggagtg attt                                              24

<210> SEQ ID NO 22
<211> LENGTH: 25
<212> TYPE: DNA
<213> ORGANISM: Homo sapiens
<220> FEATURE:
<221> NAME/KEY: misc_feature
<223> OTHER INFORMATION: SLC43A2 reverse primer

<400> SEQUENCE: 22
aaaaataacc ataaaccatc cttcc                                             25

<210> SEQ ID NO 23
<211> LENGTH: 37
<212> TYPE: DNA
<213> ORGANISM: Homo sapiens

<400> SEQUENCE: 23
gccgcagtag ttcttcagtg gcaagcttta tgtcctg                                37

<210> SEQ ID NO 24
<211> LENGTH: 37
<212> TYPE: DNA
<213> ORGANISM: Homo sapiens

<400> SEQUENCE: 24
gccgcagtaa ggtcccagtg gcaagcttta tgtcctg                                37

<210> SEQ ID NO 25
<211> LENGTH: 20
<212> TYPE: DNA
<213> ORGANISM: Homo sapiens

<400> SEQUENCE: 25
cagtggcagc tgagacctct                                                   20

<210> SEQ ID NO 26
<211> LENGTH: 19
<212> TYPE: DNA
<213> ORGANISM: Homo sapiens

<400> SEQUENCE: 26

```
ccttcttggc agctcaggg                                                     19

<210> SEQ ID NO 27
<211> LENGTH: 22
<212> TYPE: RNA
<213> ORGANISM: Homo sapiens

<400> SEQUENCE: 27
ugucaagaag uugaccgucg aa                                                 22

<210> SEQ ID NO 28
<211> LENGTH: 20
<212> TYPE: DNA
<213> ORGANISM: Homo sapiens

<400> SEQUENCE: 28
cagaaattat agagacctct                                                    20

<210> SEQ ID NO 29
<211> LENGTH: 19
<212> TYPE: DNA
<213> ORGANISM: Homo sapiens

<400> SEQUENCE: 29
ccttctaaat tatacaggg                                                     19

<210> SEQ ID NO 30
<211> LENGTH: 34
<212> TYPE: DNA
<213> ORGANISM: Homo sapiens

<400> SEQUENCE: 30
caaggaaatg tgtaggcagc tatggttgtc acag                                    34

<210> SEQ ID NO 31
<211> LENGTH: 33
<212> TYPE: DNA
<213> ORGANISM: Homo sapiens

<400> SEQUENCE: 31
caaggaatgt gtattactag atggttgtca cag                                     33
```